United States Patent
Meade et al.

(10) Patent No.: US 7,815,589 B2
(45) Date of Patent: *Oct. 19, 2010

(54) METHODS AND APPARATUS FOR ANCHORING WITHIN THE GASTROINTESTINAL TRACT

(75) Inventors: John C. Meade, Mendon, MA (US); Andy H. Levine, Newton, MA (US); David A. Melanson, Hudson, NH (US); John F. Cvinar, Winchester, MA (US)

(73) Assignee: GI Dynamics, Inc., Lexington, MA (US)

(*) Notice: Subject to any disclaimer, the term of this patent is extended or adjusted under 35 U.S.C. 154(b) by 1118 days.

This patent is subject to a terminal disclaimer.

(21) Appl. No.: 10/858,852

(22) Filed: Jun. 1, 2004

(65) Prior Publication Data
US 2005/0125020 A1    Jun. 9, 2005

Related U.S. Application Data

(60) Provisional application No. 60/528,084, filed on Dec. 9, 2003, provisional application No. 60/544,527, filed on Feb. 13, 2004.

(51) Int. Cl.
*A61M 5/00* (2006.01)
*A61F 2/04* (2006.01)

(52) U.S. Cl. ....................... 604/8; 623/23.64
(58) Field of Classification Search ............. 623/23.64, 623/1.14, 1.35; 604/8
See application file for complete search history.

(56) References Cited

U.S. PATENT DOCUMENTS

| 1,899,781 A | 2/1933 | Twiss |
| 2,464,933 A | 3/1949 | Kaslow |

(Continued)

FOREIGN PATENT DOCUMENTS

| DE | 33 26 061 A1 | 2/1984 |

(Continued)

OTHER PUBLICATIONS

Rubino, F. and J. Marescaux, "Effect of Duodenal-Jejunal Exclusion in a Non-obese Animal Model of Type 2 Diabetes, A New Perspective for an Old Disease," *Annals of Surgery* 239(1):1-11, Jan. 2004.

(Continued)

*Primary Examiner*—Thomas J Sweet
(74) *Attorney, Agent, or Firm*—Hamilton, Brook, Smith & Reynolds, P.C.

(57) ABSTRACT

The present invention relates to an anchor configured for minimally-invasive implantation and sized to remain securely positioned within at least a portion of the gastrointestinal tract of an animal. The anchor includes a radial spring formed from an elongated resilient member shaped into an annular wave pattern about a central axis. The anchor defines a central lumen and provides an outward radial force, while allowing for substantial flexure about its perimeter. The anchor is generally removable, but can include fasteners, such as barbs, to further secure it to the surrounding anatomy. In some embodiments, the anchor includes a connector coupling a fixed portion to a removable portion. Further, the anchor can be used to secure a medical device within the body, such as a flexible sleeve within the intestine.

28 Claims, 22 Drawing Sheets

U.S. PATENT DOCUMENTS

| | | | |
|---|---|---|---|
| 3,780,740 A | 12/1973 | Rhea | |
| 4,133,315 A | 1/1979 | Berman et al. | |
| 4,134,405 A | 1/1979 | Smit | |
| 4,246,893 A | 1/1981 | Berson | |
| 4,265,694 A | 5/1981 | Boretos et al. | |
| 4,270,542 A | 6/1981 | Plumley | |
| 4,271,827 A | 6/1981 | Angelchik | |
| 4,279,251 A | 7/1981 | Rüsch | |
| 4,315,509 A | 2/1982 | Smit | |
| 4,341,218 A | 7/1982 | U | |
| 4,403,604 A | 9/1983 | Wilkinson et al. | |
| 4,416,267 A | 11/1983 | Garren et al. | |
| 4,501,264 A | 2/1985 | Rockey | |
| 4,580,568 A | 4/1986 | Gianturco | |
| 4,607,618 A | 8/1986 | Angelchik | |
| 4,617,932 A | 10/1986 | Kornberg | |
| 4,641,653 A | 2/1987 | Rockey | |
| 4,648,383 A | 3/1987 | Angelchik | |
| 4,763,653 A | 8/1988 | Rockey | |
| 4,768,507 A * | 9/1988 | Fischell et al. ............. 623/1.11 |
| 4,823,808 A | 4/1989 | Clegg et al. | |
| 4,846,836 A | 7/1989 | Reich | |
| 4,878,905 A | 11/1989 | Blass | |
| 4,905,693 A | 3/1990 | Ravo | |
| 4,913,141 A | 4/1990 | Hillstead | |
| 5,035,706 A | 7/1991 | Gianturco et al. | |
| 5,037,387 A | 8/1991 | Quinn et al. | |
| 5,041,126 A | 8/1991 | Gianturco | |
| 5,057,091 A | 10/1991 | Andersen | |
| 5,059,166 A * | 10/1991 | Fischell et al. ................ 600/3 |
| 5,104,399 A | 4/1992 | Lazarus | |
| 5,123,917 A | 6/1992 | Lee | |
| 5,135,516 A | 8/1992 | Sahatjian et al. | |
| 5,152,756 A | 10/1992 | Quinn et al. | |
| 5,152,782 A | 10/1992 | Kowligi et al. | |
| 5,176,617 A * | 1/1993 | Fischell et al. ................ 600/3 |
| 5,190,561 A | 3/1993 | Graber | |
| 5,236,423 A | 8/1993 | Mix et al. | |
| 5,246,456 A | 9/1993 | Wilkinson | |
| 5,254,133 A | 10/1993 | Seid | |
| 5,279,553 A | 1/1994 | Winkler et al. | |
| 5,282,824 A | 2/1994 | Gianturco | |
| 5,290,294 A | 3/1994 | Cox et al. | |
| 5,306,300 A | 4/1994 | Berry | |
| 5,314,444 A | 5/1994 | Gianturco | |
| 5,314,472 A | 5/1994 | Fontaine | |
| 5,314,473 A | 5/1994 | Godin | |
| 5,318,530 A | 6/1994 | Nelson, Jr. | |
| 5,322,501 A | 6/1994 | Mahmud-Durrani | |
| 5,330,500 A | 7/1994 | Song | |
| 5,364,353 A | 11/1994 | Corfitsen et al. | |
| 5,387,235 A | 2/1995 | Chuter | |
| 5,389,090 A * | 2/1995 | Fischell et al. ............. 604/528 |
| 5,401,241 A | 3/1995 | Delany | |
| 5,405,378 A | 4/1995 | Strecker | |
| 5,417,697 A | 5/1995 | Wilk et al. | |
| 5,443,498 A | 8/1995 | Fontaine | |
| 5,456,713 A | 10/1995 | Chuter | |
| 5,480,423 A | 1/1996 | Ravenscroft et al. | |
| 5,492,530 A * | 2/1996 | Fischell et al. ............. 604/510 |
| 5,507,767 A | 4/1996 | Maeda et al. | |
| 5,507,771 A | 4/1996 | Gianturco | |
| 5,522,880 A | 6/1996 | Barone et al. | |
| 5,562,697 A | 10/1996 | Christiansen | |
| 5,569,219 A | 10/1996 | Hakki et al. | |
| 5,571,173 A | 11/1996 | Parodi | |
| 5,605,530 A * | 2/1997 | Fischell et al. ................ 600/3 |
| 5,607,442 A * | 3/1997 | Fischell et al. ............. 623/1.18 |
| 5,611,787 A | 3/1997 | Demeter et al. | |
| 5,624,430 A | 4/1997 | Eton et al. | |
| 5,630,797 A | 5/1997 | Diedrich et al. | |
| 5,634,928 A * | 6/1997 | Fischell et al. ............. 623/1.11 |
| 5,639,274 A * | 6/1997 | Fischell et al. ........... 604/96.01 |
| 5,643,312 A * | 7/1997 | Fischell et al. ............. 623/1.15 |
| 5,662,713 A | 9/1997 | Andersen et al. | |
| 5,665,064 A | 9/1997 | Bodicky et al. | |
| 5,669,932 A * | 9/1997 | Fischell et al. ............. 606/198 |
| 5,690,642 A | 11/1997 | Osborne et al. | |
| 5,693,084 A | 12/1997 | Chuter | |
| 5,695,516 A * | 12/1997 | Fischell et al. ............. 606/194 |
| 5,697,971 A * | 12/1997 | Fischell et al. ............. 623/1.15 |
| 5,713,948 A | 2/1998 | Uflacker | |
| 5,715,832 A | 2/1998 | Koblish et al. | |
| 5,720,776 A * | 2/1998 | Chuter et al. ............. 623/1.36 |
| 5,722,984 A * | 3/1998 | Fischell et al. ............. 606/198 |
| 5,730,698 A * | 3/1998 | Fischell et al. ................ 600/3 |
| 5,733,325 A | 3/1998 | Robinson et al. | |
| 5,735,859 A * | 4/1998 | Fischell et al. ............. 606/108 |
| 5,735,892 A | 4/1998 | Myers et al. | |
| 5,743,874 A * | 4/1998 | Fischell et al. ........... 604/103.1 |
| 5,749,825 A * | 5/1998 | Fischell et al. ................ 600/3 |
| 5,755,777 A | 5/1998 | Chuter | |
| 5,759,174 A * | 6/1998 | Fischell et al. ........... 604/103.1 |
| 5,776,186 A | 7/1998 | Uflacker | |
| 5,792,144 A * | 8/1998 | Fischell et al. ............. 606/108 |
| 5,792,172 A * | 8/1998 | Fischell et al. ............. 606/198 |
| 5,800,456 A | 9/1998 | Maeda et al. | |
| 5,800,526 A | 9/1998 | Anderson et al. | |
| 5,820,584 A | 10/1998 | Crabb | |
| 5,830,229 A | 11/1998 | Konya et al. | |
| 5,840,009 A * | 11/1998 | Fischell et al. ................ 600/3 |
| 5,843,164 A | 12/1998 | Frantzen et al. | |
| 5,855,601 A | 1/1999 | Bessler et al. | |
| 5,876,445 A | 3/1999 | Andersen et al. | |
| 5,879,282 A * | 3/1999 | Fischell et al. ................ 600/3 |
| 5,879,370 A * | 3/1999 | Fischell et al. ............. 623/1.16 |
| 5,895,391 A | 4/1999 | Farnholtz | |
| 5,910,145 A * | 6/1999 | Fischell et al. ............. 606/108 |
| 5,913,895 A * | 6/1999 | Burpee et al. ............. 623/1.2 |
| 5,919,233 A | 7/1999 | Knopf et al. | |
| 5,925,063 A | 7/1999 | Khosravi | |
| 5,962,620 A | 10/1999 | Reich et al. | |
| 5,964,771 A | 10/1999 | Beyar et al. | |
| 5,976,153 A * | 11/1999 | Fischell et al. ............. 623/1.11 |
| 6,013,019 A * | 1/2000 | Fischell et al. ................ 600/3 |
| 6,027,508 A | 2/2000 | Ren et al. | |
| 6,027,526 A | 2/2000 | Limon et al. | |
| 6,035,856 A | 3/2000 | LaFontaine et al. | |
| 6,074,673 A | 6/2000 | Guillen | |
| 6,086,604 A * | 7/2000 | Fischell et al. ............. 606/198 |
| 6,099,552 A | 8/2000 | Adams | |
| 6,102,887 A | 8/2000 | Altman | |
| 6,120,533 A * | 9/2000 | Fischell ..................... 623/1.11 |
| 6,120,534 A | 9/2000 | Ruiz | |
| 6,132,471 A | 10/2000 | Johlin, Jr. | |
| 6,146,323 A * | 11/2000 | Fischell ........................ 600/3 |
| 6,152,956 A | 11/2000 | Pierce | |
| 6,179,868 B1 * | 1/2001 | Burpee et al. ............. 623/1.17 |
| 6,190,403 B1 * | 2/2001 | Fischell et al. ............. 623/1.16 |
| 6,200,336 B1 | 3/2001 | Pavcnik et al. | |
| 6,221,043 B1 * | 4/2001 | Fischell et al. ......... 604/103.07 |
| 6,221,102 B1 | 4/2001 | Baker et al. | |
| 6,241,738 B1 | 6/2001 | Dereume | |
| 6,241,757 B1 | 6/2001 | An et al. | |
| 6,251,064 B1 | 6/2001 | Silverman et al. | |
| 6,251,132 B1 | 6/2001 | Ravenscroft et al. | |
| 6,270,521 B1 * | 8/2001 | Fischell et al. ............. 623/1.11 |
| 6,293,960 B1 | 9/2001 | Ken | |
| 6,302,891 B1 | 10/2001 | Nadal | |
| 6,302,917 B1 | 10/2001 | Dua et al. | |
| 6,315,708 B1 * | 11/2001 | Salmon et al. ................ 600/3 |
| 6,322,538 B1 | 11/2001 | Elbert et al. | |
| 6,331,190 B1 | 12/2001 | Shokoohi et al. | |
| 6,332,877 B1 | 12/2001 | Michels | |

| | | | | | | |
|---|---|---|---|---|---|---|
| 6,355,056 B1 | 3/2002 | Pinheiro | | 7,338,520 B2 | 3/2008 | Bailey et al. |
| 6,356,782 B1 | 3/2002 | Sirimanne et al. | | 7,347,875 B2 | 3/2008 | Levine et al. |
| 6,375,660 B1 * | 4/2002 | Fischell et al. .............. 606/108 | | 7,354,454 B2 | 4/2008 | Stack et al. |
| 6,383,214 B1 | 5/2002 | Banas et al. | | 7,476,256 B2 | 1/2009 | Meade et al. |
| 6,387,114 B2 | 5/2002 | Adams | | 2001/0020190 A1 | 9/2001 | Taylor |
| 6,401,718 B1 | 6/2002 | Johnson et al. | | 2002/0022853 A1 | 2/2002 | Swanson et al. |
| 6,402,779 B1 | 6/2002 | Colone et al. | | 2002/0032487 A1 | 3/2002 | Dua et al. |
| 6,406,792 B1 | 6/2002 | Briquet et al. | | 2002/0065545 A1 | 5/2002 | Leonhardt et al. |
| 6,428,558 B1 | 8/2002 | Jones et al. | | 2002/0091439 A1 | 7/2002 | Baker et al. |
| 6,450,989 B2 | 9/2002 | Dubrul et al. | | 2002/0107565 A1 | 8/2002 | Greenhalgh |
| 6,458,074 B1 | 10/2002 | Matsui et al. | | 2002/0120277 A1 | 8/2002 | Hauschild et al. |
| 6,485,409 B1 | 11/2002 | Voloshin et al. | | 2002/0143387 A1 | 10/2002 | Soetikno et al. |
| 6,485,515 B2 | 11/2002 | Strecker | | 2002/0147489 A1 | 10/2002 | Hong et al. |
| 6,508,833 B2 | 1/2003 | Pavcnik et al. | | 2002/0151953 A1 | 10/2002 | Chobotov et al. |
| 6,520,985 B1 * | 2/2003 | Burpee et al. .............. 623/1.11 | | 2002/0177890 A1 | 11/2002 | Lenker |
| 6,524,335 B1 | 2/2003 | Hartley et al. | | 2002/0183768 A1 | 12/2002 | Deem et al. |
| 6,524,336 B1 | 2/2003 | Papazolgou et al. | | 2002/0183786 A1 | 12/2002 | Girton |
| 6,530,951 B1 | 3/2003 | Bates et al. | | 2002/0188344 A1 | 12/2002 | Bolea et al. |
| 6,537,247 B2 | 3/2003 | Shannon | | 2002/0193828 A1 | 12/2002 | Griffin et al. |
| 6,540,775 B1 * | 4/2003 | Fischell et al. .............. 623/1.15 | | 2003/0032941 A1 | 2/2003 | Boyle et al. |
| 6,540,789 B1 | 4/2003 | Silverman et al. | | 2003/0040804 A1 | 2/2003 | Stack et al. |
| 6,544,291 B2 | 4/2003 | Taylor | | 2003/0040808 A1 | 2/2003 | Stack et al. |
| 6,547,817 B1 * | 4/2003 | Fischell et al. .............. 623/1.16 | | 2003/0050684 A1 | 3/2003 | Abrams et al. |
| 6,558,400 B2 | 5/2003 | Deem et al. | | 2003/0109892 A1 | 6/2003 | Deem et al. |
| 6,558,429 B2 | 5/2003 | Taylor | | 2003/0109931 A1 | 6/2003 | Geitz |
| 6,565,597 B1 | 5/2003 | Fearnot et al. | | 2003/0109935 A1 | 6/2003 | Geitz |
| 6,589,213 B2 | 7/2003 | Reydel | | 2003/0120265 A1 | 6/2003 | Deem et al. |
| 6,589,275 B1 | 7/2003 | Ivancev et al. | | 2003/0149467 A1 | 8/2003 | Linder et al. |
| 6,623,518 B2 | 9/2003 | Thompson et al. | | 2003/0153927 A1 | 8/2003 | DiPoto et al. |
| 6,635,069 B1 | 10/2003 | Teoh et al. | | 2003/0191476 A1 | 10/2003 | Smit |
| 6,635,079 B2 | 10/2003 | Unsworth et al. | | 2003/0199989 A1 | 10/2003 | Stack et al. |
| 6,645,239 B1 | 11/2003 | Park et al. | | 2003/0199990 A1 | 10/2003 | Stack et al. |
| 6,652,555 B1 | 11/2003 | VanTassel et al. | | 2003/0199991 A1 | 10/2003 | Stack et al. |
| 6,656,194 B1 | 12/2003 | Gannoe et al. | | 2003/0208260 A1 | 11/2003 | Lau et al. |
| 6,669,722 B2 * | 12/2003 | Chen et al. .................. 623/1.15 | | 2003/0216749 A1 | 11/2003 | Ishikawa et al. |
| 6,675,809 B2 | 1/2004 | Stack et al. | | 2003/0233140 A1 | 12/2003 | Hartley et al. |
| 6,676,692 B2 | 1/2004 | Rabkin et al. | | 2004/0019388 A1 | 1/2004 | Starkebaum |
| 6,695,875 B2 | 2/2004 | Stelter et al. | | 2004/0024386 A1 | 2/2004 | Deem et al. |
| 6,699,263 B2 | 3/2004 | Cope | | 2004/0037865 A1 | 2/2004 | Miller |
| 6,699,278 B2 * | 3/2004 | Fischell et al. .............. 623/1.15 | | 2004/0039452 A1 | 2/2004 | Bessler |
| 6,706,061 B1 * | 3/2004 | Fischell et al. .............. 623/1.15 | | 2004/0044357 A1 | 3/2004 | Gannoe et al. |
| 6,716,240 B2 * | 4/2004 | Fischell et al. .............. 623/1.16 | | 2004/0082963 A1 | 4/2004 | Gannoe et al. |
| 6,736,840 B2 * | 5/2004 | Fischell et al. .............. 623/1.11 | | 2004/0092892 A1 | 5/2004 | Kagan et al. |
| 6,740,121 B2 | 5/2004 | Geitz | | 2004/0092974 A1 | 5/2004 | Gannoe et al. |
| 6,755,869 B2 | 6/2004 | Geitz | | 2004/0093065 A1 | 5/2004 | Yachia et al. |
| 6,764,518 B2 | 7/2004 | Godin | | 2004/0098079 A1 | 5/2004 | Hartley et al. |
| 6,773,440 B2 | 8/2004 | Gannoe et al. | | 2004/0107004 A1 | 6/2004 | Levine et al. |
| 6,776,791 B1 | 8/2004 | Stallings et al. | | 2004/0117004 A1 | 6/2004 | Osborne et al. |
| 6,802,868 B2 | 10/2004 | Silverman et al. | | 2004/0117031 A1 | 6/2004 | Stack et al. |
| 6,821,291 B2 | 11/2004 | Bolea et al. | | 2004/0122452 A1 | 6/2004 | Deem et al. |
| 6,845,776 B2 | 1/2005 | Stack et al. | | 2004/0122453 A1 | 6/2004 | Deem et al. |
| 6,860,901 B1 | 3/2005 | Baker et al. | | 2004/0122470 A1 | 6/2004 | Deem et al. |
| 6,936,065 B2 * | 8/2005 | Khan et al. .................. 623/1.11 | | 2004/0133147 A1 | 7/2004 | Woo |
| 6,960,233 B1 | 11/2005 | Berg et al. | | 2004/0136971 A1 | 7/2004 | Scharp et al. |
| 7,011,673 B2 * | 3/2006 | Fischell et al. .............. 623/1.11 | | 2004/0138525 A1 | 7/2004 | Saadat et al. |
| 7,025,791 B2 | 4/2006 | Levine et al. | | 2004/0138529 A1 | 7/2004 | Wiltshire et al. |
| 7,033,384 B2 | 4/2006 | Gannoe et al. | | 2004/0138760 A1 | 7/2004 | Schurr |
| 7,037,327 B2 * | 5/2006 | Salmon et al. .............. 623/1.11 | | 2004/0138761 A1 | 7/2004 | Stack et al. |
| 7,037,344 B2 | 5/2006 | Kagan et al. | | 2004/0143342 A1 | 7/2004 | Stack et al. |
| 7,081,132 B2 | 7/2006 | Cook et al. | | 2004/0148034 A1 | 7/2004 | Kagan et al. |
| 7,087,088 B2 | 8/2006 | Berg et al. | | 2004/0153167 A1 | 8/2004 | Stack et al. |
| 7,121,283 B2 | 10/2006 | Stack et al. | | 2004/0158229 A1 | 8/2004 | Quinn |
| 7,122,058 B2 | 10/2006 | Levine et al. | | 2004/0158331 A1 | 8/2004 | Stack et al. |
| 7,146,984 B2 | 12/2006 | Stack et al. | | 2004/0172063 A1 | 9/2004 | Li et al. |
| 7,152,607 B2 | 12/2006 | Stack et al. | | 2004/0172088 A1 | 9/2004 | Knudson et al. |
| 7,160,312 B2 | 1/2007 | Saadat | | 2004/0172141 A1 | 9/2004 | Stack et al. |
| 7,175,660 B2 | 2/2007 | Cartledge et al. | | 2004/0172142 A1 | 9/2004 | Stack et al. |
| 7,211,114 B2 | 5/2007 | Bessler et al. | | 2004/0172143 A1 | 9/2004 | Geitz |
| 7,220,237 B2 | 5/2007 | Gannoe et al. | | 2004/0181242 A1 | 9/2004 | Stack et al. |
| 7,220,284 B2 | 5/2007 | Kagan et al. | | 2004/0193093 A1 | 9/2004 | Desmond, III |
| 7,267,694 B2 | 9/2007 | Levine et al. | | 2004/0193261 A1 | 9/2004 | Berreklouw |
| 7,314,489 B2 | 1/2008 | McKenna et al. | | 2004/0220682 A1 | 11/2004 | Levine et al. |
| 7,329,285 B2 | 2/2008 | Levine et al. | | 2004/0236401 A1 | 11/2004 | Shin et al. |

| | | | | | | |
|---|---|---|---|---|---|---|
| 2004/0249362 | A1 | 12/2004 | Levine et al. | WO | WO 00/28922 A1 | 5/2000 |
| 2005/0004681 | A1 | 1/2005 | Stack et al. | WO | WO 00/32137 | 6/2000 |
| 2005/0043601 | A1 | 2/2005 | Kilcoyne et al. | WO | WO 00/42945 A1 | 7/2000 |
| 2005/0043817 | A1 | 2/2005 | McKenna et al. | WO | WO 00/42949 | 7/2000 |
| 2005/0049718 | A1 | 3/2005 | Dann et al. | WO | WO 01/12256 A1 | 2/2001 |
| 2005/0055039 | A1 | 3/2005 | Burnett et al. | WO | WO 01/35861 A1 | 5/2001 |
| 2005/0075622 | A1 | 4/2005 | Levine et al. | WO | WO 01/45485 A2 | 6/2001 |
| 2005/0080395 | A1 | 4/2005 | Levine et al. | WO | WO 02/081019 A1 | 10/2002 |
| 2005/0080431 | A1 | 4/2005 | Levine et al. | WO | WO 02/096327 A2 | 12/2002 |
| 2005/0080491 | A1 | 4/2005 | Levine et al. | WO | WO 03/017882 A2 | 3/2003 |
| 2005/0085787 | A1 | 4/2005 | Laufer | WO | WO 03/086246 A1 | 10/2003 |
| 2005/0085923 | A1 | 4/2005 | Levine et al. | WO | WO 03/086247 A1 | 10/2003 |
| 2005/0090873 | A1 | 4/2005 | Imran | WO | WO 03/086360 A1 | 10/2003 |
| 2005/0096750 | A1 | 5/2005 | Kagan et al. | WO | WO 03/094785 A1 | 11/2003 |
| 2005/0125020 | A1 | 6/2005 | Meade et al. | WO | WO 2004/000169 A1 | 12/2003 |
| 2005/0125075 | A1 | 6/2005 | Meade et al. | WO | WO 2004/004542 A2 | 1/2004 |
| 2005/0149114 | A1 | 7/2005 | Cartledge et al. | WO | WO 2004/004542 A3 | 1/2004 |
| 2005/0171556 | A1 | 8/2005 | Murphy | WO | WO 2004/014237 A1 | 2/2004 |
| 2005/0192614 | A1 | 9/2005 | Binmoeller | WO | WO 2004/019765 A2 | 3/2004 |
| 2005/0216040 | A1 | 9/2005 | Gertner et al. | WO | WO 2004/019765 A3 | 3/2004 |
| 2005/0216042 | A1 | 9/2005 | Gertner | WO | WO 2004/021894 A1 | 3/2004 |
| 2005/0221072 | A1 | 10/2005 | Dubrow et al. | WO | WO 2004/037064 A2 | 5/2004 |
| 2005/0228415 | A1 | 10/2005 | Gertner | WO | WO 2004/037064 A3 | 5/2004 |
| 2005/0228504 | A1 | 10/2005 | Demarais | WO | WO 2004/049982 A2 | 6/2004 |
| 2005/0240279 | A1 | 10/2005 | Kagan et al. | WO | WO 2004/064680 A1 | 8/2004 |
| 2005/0256587 | A1 | 11/2005 | Egan | WO | WO 2004/064682 A1 | 8/2004 |
| 2005/0267499 | A1 | 12/2005 | Stack et al. | WO | WO 2004/064685 A1 | 8/2004 |
| 2005/0267533 | A1 | 12/2005 | Gertner | WO | WO 2004/069331 A2 | 8/2004 |
| 2006/0009858 | A1 | 1/2006 | Levine et al. | WO | WO 2004/069332 A1 | 8/2004 |
| 2006/0064120 | A1 | 3/2006 | Levine et al. | WO | WO 2004/073782 A1 | 9/2004 |
| 2006/0106332 | A1 | 5/2006 | Knudson et al. | WO | WO 2004/087014 A2 | 10/2004 |
| 2006/0155312 | A1 | 7/2006 | Levine et al. | WO | WO 2004/087233 A2 | 10/2004 |
| 2006/0161139 | A1 | 7/2006 | Levine et al. | WO | WO 2004/093639 A2 | 11/2004 |
| 2006/0161172 | A1 | 7/2006 | Levine et al. | WO | WO 2004/093639 A3 | 11/2004 |
| 2006/0161187 | A1 | 7/2006 | Levine et al. | WO | WO 2005/011533 A1 | 2/2005 |
| 2006/0161265 | A1 | 7/2006 | Levine et al. | WO | WO 2005/060869 A1 | 7/2005 |
| 2006/0212042 | A1 | 9/2006 | Lamport et al. | WO | WO 2005/060882 A1 | 7/2005 |
| 2006/0265082 | A1 | 11/2006 | Meade et al. | WO | WO 2005/082296 A1 | 9/2005 |
| 2006/0271175 | A1 | 11/2006 | Woolfson et al. | WO | WO 2005/110280 A2 | 11/2005 |
| 2006/0287734 | A1 | 12/2006 | Stack et al. | WO | WO 2005/117716 A2 | 12/2005 |
| 2007/0005147 | A1 | 1/2007 | Levine et al. | WO | WO 2005/118049 A1 | 12/2005 |
| 2007/0010864 | A1 | 1/2007 | Dann et al. | WO | WO 2005/120363 A1 | 12/2005 |
| 2007/0027548 | A1 | 2/2007 | Levine et al. | WO | WO 2006/016894 A1 | 2/2006 |
| 2007/0032879 | A1 | 2/2007 | Levine et al. | WO | WO 2006/034062 A1 | 3/2006 |
| 2007/0049801 | A1 | 3/2007 | Lamport et al. | WO | WO 2006/078781 A1 | 7/2006 |
| 2007/0083271 | A1 | 4/2007 | Levine et al. | WO | WO 2006/078927 A1 | 7/2006 |
| 2008/0071383 | A1 | 3/2008 | Levine et al. | WO | WO 2006/088578 A1 | 8/2006 |
| 2008/0097466 | A1 | 4/2008 | Levine et al. | WO | WO 2006/102012 A1 | 9/2006 |
| 2008/0103604 | A1 | 5/2008 | Levine et al. | WO | WO 2006/133311 A2 | 12/2006 |
| 2008/0208357 | A1 | 8/2008 | Melanson et al. | | | |
| 2008/0223476 | A1 | 9/2008 | Stinson | | | |
| 2008/0234834 | A1 | 9/2008 | Meade et al. | | | |

FOREIGN PATENT DOCUMENTS

| | | |
|---|---|---|
| EP | 0 480 667 B1 | 4/1992 |
| EP | 0278937 B1 | 10/1993 |
| EP | 0 686 379 A2 | 12/1995 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| EP | 1 504 778 A2 | 2/2005 |
| EP | 1 504 778 A3 | 3/2005 |
| JP | 04212348 | 8/1992 |
| JP | 08-052165 | 2/1996 |
| JP | 2005-021504 | 1/2005 |
| WO | WO 92/06734 A1 | 4/1992 |
| WO | WO 97/03624 A1 | 2/1997 |
| WO | WO 00/12027 | 3/2000 |

OTHER PUBLICATIONS

Yates III, M. R., et al., "Palliation of Malignant Gastric and Small Intestinal Strictures With Self-Expandable Metal Stents," *Endoscopy* 30:266-272 (1998).

Bethge, N., et al., "Human tissue responses to metal stents implanted in vivo for the palliation of malignant stenoses," *Gastrointestinal Endoscopy* 43(6):596-602 (1996).

Binkert, C. A., et al., "Benign and Malignant Stenoses of the Stomach and Duodenum: Treatment with Self-expanding Metallic Endoprostheses," *Radiology* 199(2):335-338 (1996).

Cwikiel, W., et al., "Self-expanding Stent in the Treatment of Benign Esophageal Strictures: Experimental Study in Pigs and Presentation of Clinical Cases," *Radiology* 187(3):667-671 (1993).

Dolan, K. et al., "Treating Diabetes in the Morbidly Obese by Laparoscopic Gastric Band," *Obesity Surgery*, vol. 13, pp. 439-443 (2003).

Park, B.P. et al., Malignant Obstruction of Gastric Outlet and Duodenum: Palliation with Flexible Covered Metallic Stents, *Radiology* 219(3):679-683 (2001).

Dormann, A.J. et al., "Self-expanding metallic stents for continous dilatation of benign stenosis in gastrointestinal tract—first results of long-term follow-up in interim stent application in pyloric and colonic obstructions," *Z Gastroenteral* 39:957-960 (2001).

Pories, W.J., "Why Does the Gastric Bypass Control Type 2 Diabetes Mellitus?" *Obesity Surgery*, 2:303-313 (1992).

Pories, W.J., et al., "Etiology of Type II Diabetes Mellitus: Role of the Foregut," *World J. Surg.*, 25:527-531 (2001).

Rubino, F., et al., "Potential of Surgery for Curing Type 2 Diabetes Mellitus," *Annals of Surgery* 236(5): 554-559 (2002).

Sandha, G. S. and Marcon, N. E., "Expandable Metal Stents for Benign Esophageal Obstruction," Gastrointestinal Endoscopy Clinics of North America 9:(3)437-446 (1999).

Feretis, C., et al., "Palliation of Malignant Gastric Outlet Obstruction with Self-Expanding Metal Stents," Endoscopy 28:225-228 (1996).

Parodi, J.C., M.D., "Endovascular Repair of Abdominal Aortic Aneurysms," *Advances in Vascular Surgery*, vol. 1, pp. 85-105 (1993).

Choostent™, Covered Esophageal Stent, Instructions, Retrieved from the Internet (http://mitech.co.kr/uploads/images/282/use guide esophachoo_english.pdf) on Jul. 26, 2005.

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul.-Aug. 1995).

Lee, S.H., "The Role of Oesophageal Stenting in the Non-Surgical Management of Oesophageal Strictures," *British J. Radiology*, 74:891-900 (Oct. 2001).

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Yoon, C.J., et al., "Removal of Retrievable Esophageal and Gastrointestinal Stents: Experience in 113 Patients," *American J. of Roentgenology*, 183:1437-1444 (Nov. 2004).

* cited by examiner

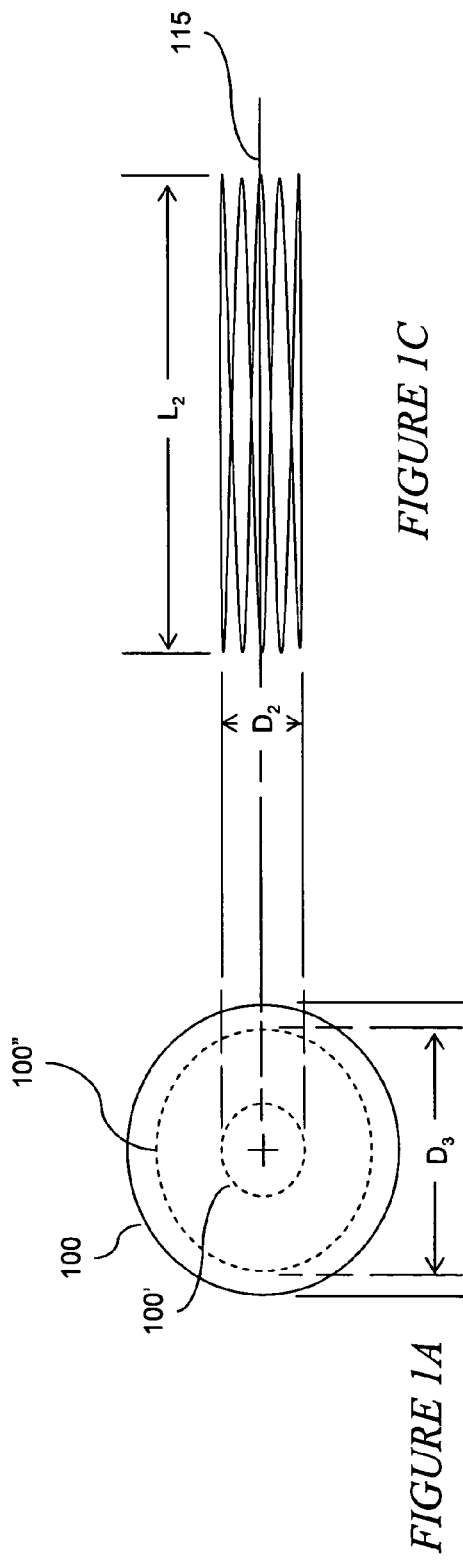
FIGURE 1A
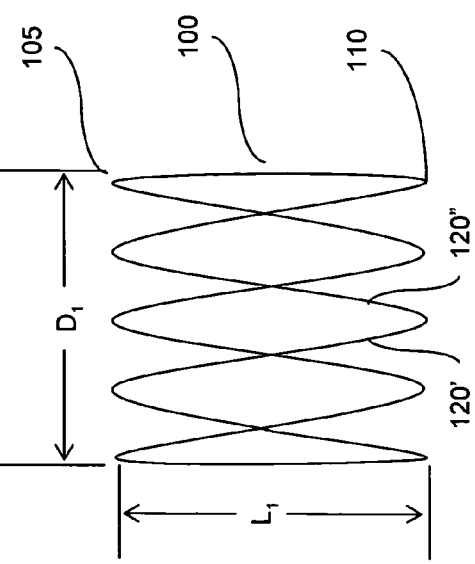
FIGURE 1B
FIGURE 1C

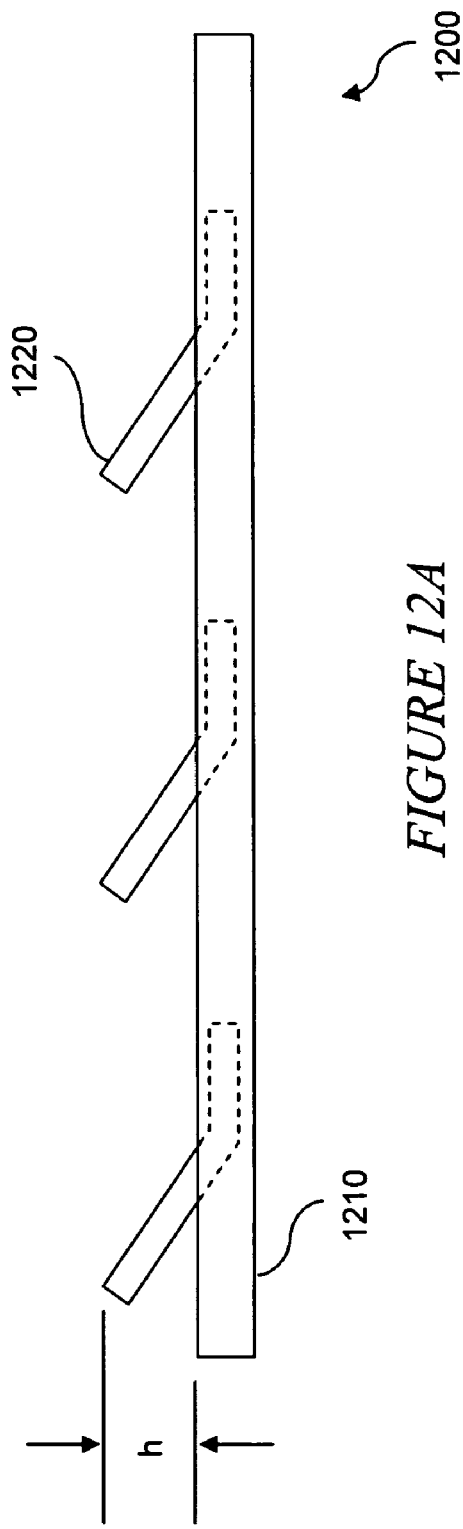
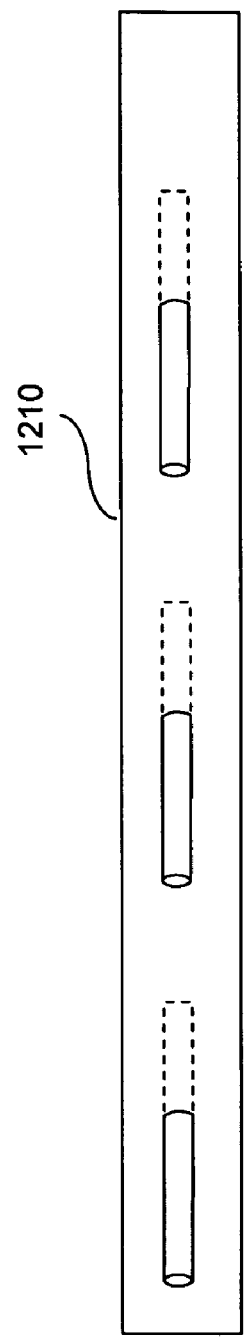
FIGURE 12A
FIGURE 12B

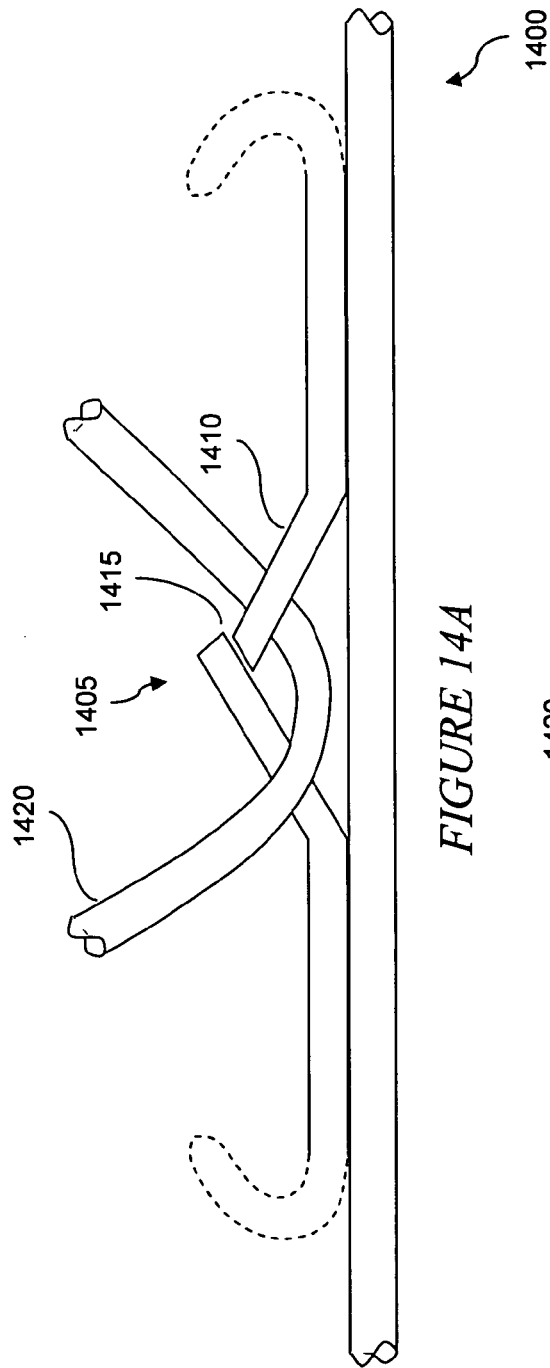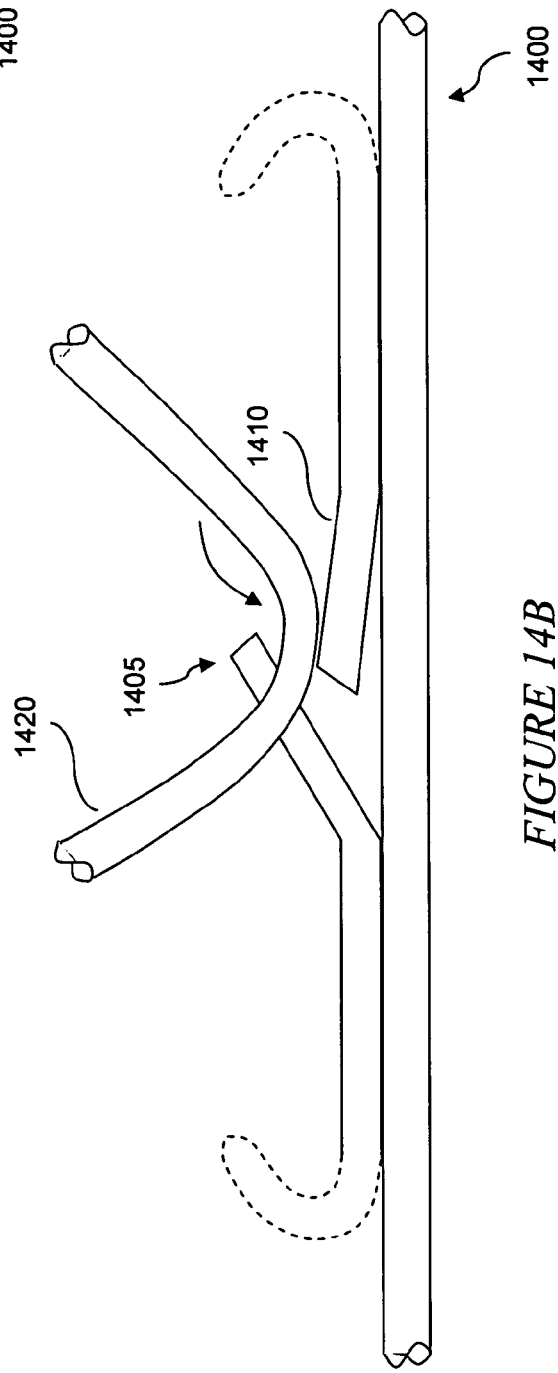

METHODS AND APPARATUS FOR ANCHORING WITHIN THE GASTROINTESTINAL TRACT

RELATED APPLICATIONS

This application claims the benefit of U.S. Provisional Application No. 60/528,084, filed on Dec. 9, 2003; and U.S. Provisional Application No. 60/544,527, filed on Feb. 13, 2004. The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the U.S. with a Body Mass Index (BMI) of 30 or above. The BMI is defined as a person's weight (in kilograms) divided by height (in meters), squared. To be considered clinically, morbidly obese, one must meet at least one of three criteria: (i) BMI over 35; (ii) 100 lbs. overweight; or (iii) 100% above an "ideal" body weight. There is also a category for the super-obese for those weighing over 350 lbs.

Obesity is an overwhelming health problem. Because of the enormous strain associated with carrying this excess weight, organs are affected, as are the nervous and circulatory systems. In 2000, the National Institute of Diabetes, Digestive and Kidney Diseases (NIDDK) estimated that there were 280,000 deaths directly related to obesity. The NIDDK further estimated that the direct cost of healthcare in the U.S. associated with obesity is $51 billion. In addition, Americans spend $33 billion per year on weight loss products. In spite of this economic cost and consumer commitment, the prevalence of obesity continues to rise at alarming rates. From 1991 to 2000, obesity in the U.S. grew by 61%. Not exclusively a U.S. problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon.

Devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices have not been successfully implemented.

SUMMARY OF THE INVENTION

One of the primary challenges in using medical devices to treat obesity is securing the device within the gastrointestinal tract. The natural lumens of the esophagus, stomach, and intestine provide relatively large diameters compared to the dimensions of delivery devices, such as endoscopes and/or catheters that are sized to minimize trauma to the natural lumen. Further complicating matters are the natural muscular contractions of that portion of the anatomy that subject devices implanted therein to substantial stresses and strains. Additionally, other forces such as gas bubbles within the intestine can compound matters by further increasing a local diameter of the intestine.

Thus, the combination of the large, varying diameters and muscular contractions tend to dislodge devices implanted therein. Additionally, the natural peristaltic contractions of the intestine attempt to push any device implanted therein either distally along with the normal passage of chyme, or proximally due to retrograde contractions.

Non-surgical methods of implantation, such as endoluminal placement are attractive, but offer further challenges for inserting devices configured to attach to such large-diameter lumens. These devices have installed diameters of about 20-30 millimeters (mm) and are preferably inserted through substantially smaller apertures. Minimally-invasive techniques for accessing the gastrointestinal tract include insertion through natural body lumens (e.g., per-oral, per-rectal). Further, to reduce trauma to the lumen, the access channel is preferably smaller in diameter than the lumen itself. Thus, access to the intestine may be limited by the interior diameter of a working catheter, or about 12 mm.

The present invention solves these problems by providing an anchor configured for catheter-based implantation and sized to remain securely positioned within at least a portion of the gastrointestinal tract, including the intestine. The anchor includes a radial spring formed from an elongated resilient member shaped into an annular wave pattern about a central axis. Thus, the anchor provides an outward radial force, but allows substantial flexure about its perimeter. Such flexure is important to allow catheter-based delivery and to provide compliance, thereby ensuring that the device will conform to the surrounding anatomical structure.

The annular wave element defines a lumen along its central axis formed between two open ends of the anchor. When implanted, the central axis of the anchor is substantially aligned with the central axis of the gastrointestinal tract, allowing chyme to pass through the device. Additionally, the anchoring device minimizes trauma to the tissue by providing sufficient flexibility and compliance, which minimizes the likelihood of tissue erosion and yet provides a solid anchoring and sealing point in the tissue.

The anchor can be removably attached within the body using mechanical fasteners such as barbs, surgical staples, and sutures and/or other fasteners, such as surgical adhesives. In an alternative embodiment, the anchor includes a portion that is fixedly attached within the body. A connector can also be provided and configured to attach a removable portion to the fixed portion. At least one application includes the treatment of obesity. Additional applications include the treatment of intestinal disorders. For these applications, the anchor enables a sleeve, or barrier, to be securely implanted within the intestine. When implanted, the sleeve acts to block the uptake of food in that portion of the intestine and/or the triggering of normal hormone response to food.

The invention relates to a gastrointestinal implant device including a wave anchor compressible in a radial direction. The wave anchor is formed by an elongated resilient member about a central axis and defines a central lumen. The resilient member defines an oscillating pattern between the first end and the second end of the device. The wave anchor is configured for insertion within a natural lumen of a gastrointestinal tract of an animal body. The central lumen can be the intestine, such as the esophagus, the stomach, the duodenum, the jejunum, the ileum and/or the colon.

In some embodiments, the oscillating pattern of the wave anchor has at least four oscillations. Generally, the resilient member is formed from a metal, an alloy, a plastic, or combinations of these materials. For example, the resilient member can include a shape-memory alloy, such as a Nickel-Titanium alloy commonly referred to as Nitinol.

In some embodiments, the elongated resilient member includes a plurality of strands. Moreover, some of the plurality of strands can have different physical properties. More generally, the elongated resilient member can include a first length having an associated physical property and a second length having a different associated physical property. For example, the physical property can be resiliency, thickness, and/or cross-sectional profile.

The central lumen of the wave anchor defines a diameter that is variable between a relaxed state and a compressed state. Also, an axial length separates the first end and second end of the anchor. Notably, the ratio of the implanted axial length to diameter ratio is at least about one (e.g., 30×30 mm, or 40×40 mm). In a relaxed state (i.e., before implantation) the length-to-diameter ratio can be as low as 0.8. In some embodiments, the relaxed diameter is about 45 mm, which compresses to about 30 mm when implanted.

Further, the device can include a feature for securing the wave anchor within a natural lumen of the gastrointestinal tract. For example, the feature can include an interference fit formed between the wave anchor and the natural lumen. Alternatively, or in addition, the feature can include a mechanical fastener, a chemical fastener, or combinations thereof. Chemical fasteners include surgical adhesive; whereas, mechanical fasteners include barbs, sutures, staples, and combinations thereof.

In some embodiments, the implant device is secured within the natural lumen using a number of barbs. These barbs can be arranged around one of the ends of the device. Further, the implant device can also be secured using a number of barbs arranged around the same end, or the other end of the device. Generally, each barb includes an elongated member, attached at one end to the device with its other end extending away from the device being sized to engage muscular tissue of the natural lumen. In some embodiments, the barbs are bioerodible. Such bioerodible barbs are well suited for implantation as they serve to temporarily secure an anchor to the surrounding tissue. Then, after degrading, the anchor is free to detach, and for intestinal applications, natural peristalsis can assist in removing the anchor from the body without the need for a second surgical procedure.

The invention also relates to a method of treatment using an unsupported, flexible sleeve having a wave anchor coupled to its proximal end. The sleeve is configured for implantation into a natural lumen of a gastrointestinal tract of an animal body.

Further, the invention relates to a gastrointestinal implant device including a first annular element configured for insertion into a natural lumen of a gastrointestinal tract of an animal, a fastener for fixedly securing the first annular element within the natural lumen, a gastrointestinal implant, and a connector for removably coupling between the first annular element and the gastrointestinal implant. The fastener can be a mechanical fastener, a chemical fastener, and combinations thereof. For example, the mechanical fastener can be one or more barbs, sutures, staples, and combinations thereof.

Additionally the gastrointestinal implant can include a second annular element. The second annular element can include an elongated sleeve having a proximal end and a distal end and defining a central lumen therebetween. The connector can be a clasp attached to one of the first annular element and the gastrointestinal implant and configured for engaging a feature of the other of the first annular element and the gastrointestinal implant. Alternatively, or in addition, the connector can be actuated by magnetic attraction. For example, the connector can include a magnet attached to one of the first annular element and the gastrointestinal implant and configured for engaging a feature of the other of the first annular element and the gastrointestinal implant.

Still further, the invention relates to a process for implanting a gastrointestinal device. The process includes inserting a first annular element into a natural lumen of a gastrointestinal tract of an animal. The first annular element is then fixedly secured within the natural lumen. Next, a gastrointestinal implant is provided and removably coupled to the first annular element. Notably, fixedly securing the first annular element can include providing a fastener, such as a mechanical fastener, a chemical fastener, or combinations thereof. For example, the mechanical fastener can be a barb, a suture, a staple, or combinations of any of these fasteners.

In some embodiments, the gastrointestinal implant includes a second annular element, such as an elongated sleeve having a proximal end and a distal end and defining a central lumen therebetween.

Removably coupling can include providing a clasp, attaching the clasp to one of the first annular element and the gastrointestinal implant, and engaging with the clasp a feature of the other of the first annular element and the gastrointestinal implant. Alternatively, or in addition, removably coupling includes providing a connector actuated by magnetic attraction. The connector is coupled to one of the first annular element and the gastrointestinal implant, and magnetically engages a connector a feature of the other of the first annular element and the gastrointestinal implant.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 1A and 1B are respectively schematic diagrams of an end-view and a side view of one embodiment of the invention in a relaxed state;

FIG. 1C is a schematic diagram of a side view of the embodiment of the invention illustrated in FIGS. 1A-1B in a compressed state;

FIGS. 12A-12B are more detailed schematic diagrams of yet another alternative embodiment of sleeve barbs;

FIGS. 14A-14B are schematic diagrams respectively of an embodiment of a connector engaged, and engaging;

DETAILED DESCRIPTION OF THE INVENTION

Figure 2A:
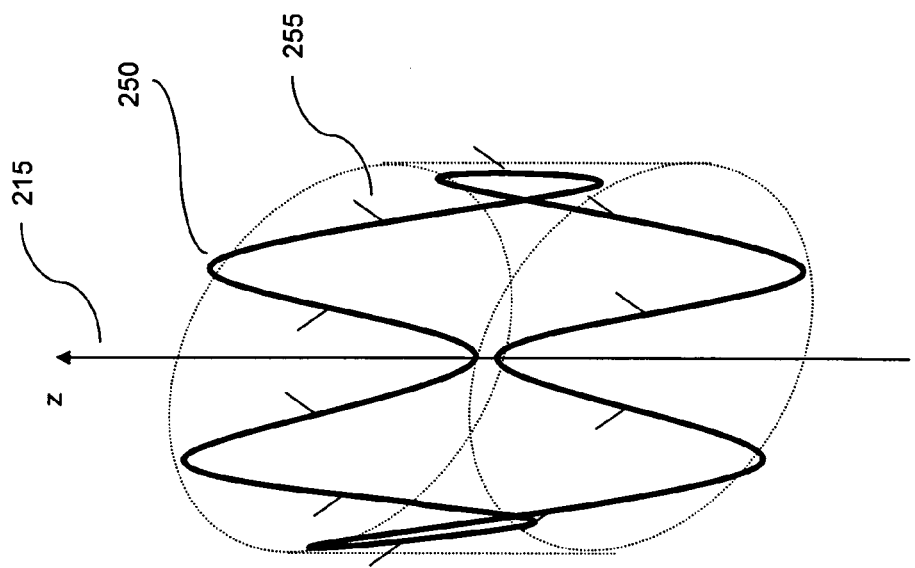
FIG. 2A is a schematic diagram of a perspective view of the invention illustrated in FIGS. 1A-1B.

A description of preferred embodiments of the invention follows.

The present invention relates to an anchor configured for minimally-invasive implantation and sized to remain securely positioned within at least a portion of the gastrointestinal tract of an animal. The anchor includes a radial spring formed from an elongated resilient member shaped into an annular wave pattern about a central axis. Thus, the anchor provides an outward radial force, but allows substantial flexure about its perimeter. Such flexure is important to allow catheter-based delivery (e.g., endoluminal) and to provide compliance, thereby ensuring that the device will conform to the surrounding anatomical structure.

When implanted, the central axis of the anchor is substantially aligned with the central axis of the gastrointestinal tract allowing chyme to pass through the device. Further, the device is resilient and sized to fit snugly within the intestine, yet compliant enough to allow the intestine to flex. Further, the wave pattern allows for radial compression of the anchor by a substantial amount thereby allowing it to fit within a working channel of catheter. Still further, the anchor presents a small surface area in contact with the intestine to minimize irritation.

The anchor can be removably attached within the body using mechanical fasteners such as barbs, surgical staples, and sutures and/or other fasteners, such as surgical adhesives. In an alternative embodiment, the anchor includes a fixed portion fixedly attached within the body and a connector configured to removably couple to a removable portion. At least one application includes the treatment of obesity and other intestinal disorders. For these applications, the anchor enables a sleeve, or barrier, to be securely implanted within the intestine. When implanted, the sleeve can act to block the uptake of food for that portion of the intestine covered by the sleeve.

Still further, the anchoring device is designed to minimize trauma to the tissue by providing sufficient flexibility and compliance. Thus, the anchoring device minimizes the likelihood of tissue erosion, while providing a solid anchoring point in the tissue. In fact, it is possible to vary the compliance of the anchoring devices quite readily by varying at least one of the material, shape, and/or dimensions.

One embodiment of a device configured for insertion within a natural lumen of a gastrointestinal tract of an animal body is shown in FIGS. 1A and 1B. The device includes a radial spring 100 including an elongated resilient member formed about a central axis 115 and defining a central lumen. The radial spring 100 has a first end 105 and a second end 110 separated along the axis 115. Notably, the resilient member defines an oscillating pattern between the first end and the second ends 105, 110. In one embodiment, the radial spring 100 referred to generally as an anchor 100 includes a number of interconnected segments, legs, or struts 120', 120" (generally 120). For example, the anchor 100 shown includes ten legs 120.

Beneficially, the wave anchor implanted in a natural lumen adjusts to the diameter of the surrounding anatomy. Exemplary relaxed diameter $D_1$ can range from a substantial diameter of about 25 to 45 mm, representing the size of an adult human's intestine. Advantageously, the radial spring is collapsible, capable of being compressed from the relaxed diameter $D_1$ to an exemplary compressed diameter $D_2$ of about 12 mm, or even less. Once inserted at a desired location within the natural lumen, the external force can be released, allowing the radial spring 100 to expand to a deployed state. Ideally, the deployed diameter $D_3$ of the radial spring 100 is between the relaxed diameter $D_1$ and the compressed diameter $D_2$, such that the radial spring 100 provides a biasing outward force against the natural lumen.

A schematic diagram of a side view of the embodiment of the invention in a compressed state is shown in FIG. 1C. As shown in the figures, the geometry of the radial spring 100 lends itself to providing a substantial ratio of the diameters between the relaxed spring state and the compressed spring state. For example, this ratio of the diameters can be substantial, such as 2-to-1 to greater than 3-to-1. Further, the two ends 105, 110 of the radial spring 100 are separated by a distance $L_1$ in its relaxed state, and a slightly longer distance $L_2$ in its compressed state. A minimum length of the anchor can be selected to provide resistance to twisting, tending to keep the central axis of the anchor substantially aligned with the central axis of the natural lumen within which it is implanted. Further, a maximum length of the anchor can also be selected to ensure that the anchor is no longer than necessary, for example, to prevent blockage of the bile duct opening when implanted in the proximal duodenum. Exemplary relaxed lengths $L_1$ can range from about 1 to 2 inches. In some embodiments, the $L_1$ is between about 1.25 and 1.5 inches. Additionally, the wave anchor can be tapered so that one end is larger than the other end (e.g., the proximal opening is larger than the distal opening). Tapering in this manner provides some resistance to the device moving proximally and reinforces engagement of any proximally-located barbs with the surrounding tissue. Thus, for an anchor implanted within the duodenum, the tapered profile would resist the anchor from migrating through the pylorus and into the stomach.

The outward force of the radial spring can be controlled by the dimensions and material used. In some applications, the radial spring 100 provides an anchor for securing a medical device within the gastrointestinal tract. For example, the anchor can be used for securing a feeding tube. In some applications, such as those intended for insertion within an intestine, the dilation force is sufficient to maintain the anchor 100 in communication with the lumen of the intestine at all times, yet not too great to cause substantial irritation to the surrounding tissue. Further, the less dilation force of the anchor, the less likely the device will erode through the tissue.

The compliance of the anchor 100 is selectable depending upon the number of nodes (pitch) and the diameter of the filament or wire used. Generally, the more nodes included in the oscillating pattern, the more compliant the device will be. Additionally, the larger the filament or wire diameter, the less compliant the device will be. In some embodiments, such as laser-cut devices, both the width and thickness of the wire (e.g., rectangular profile) can be varied. Thus, the overall compliance of the device is determined at least from the wave pattern and the wire shape and/or diameter. In some embodiments, the radial spring uses 0.012-0.020 inches diameter wire and at least five nodes.

A perspective view of one embodiment of a wave anchor 200 is shown in FIG. 2A. A central lumen defined by the wave anchor 200 is aligned with the z-axis 215. The wave pattern is generally formed along an imaginary cylinder residing at a predetermined radial distance from the z-axis 215. The wave shape extends between maximum and minimum values along the z-axis 215. Notably, the wave anchor 200 can include a number of nodes, such as the five nodes illustrated. Generally, more than three nodes are used to define a central lumen. Also, as shown, the two ends of the element forming the wave anchor 200 can be joined or otherwise coupled together at a joint 225. A weld, a bond, a mechanical crimp, a constricting sleeve, and combinations thereof can be used to form the joint 225.

The wave anchor 200 can be formed from a single filament, such as a single strand of solid wire. Alternatively, the wave anchor 200 can be formed from a number of filaments, such as a multi-stranded wire. Additionally, the individual strands of the multi-stranded wire can be selected to have different physical properties (e.g., diameter, resilience). Thus, the overall compliance and resilience of the wave anchor 200 can be controlled by selecting and combining individual strands having different properties. Further, the wave anchor 200 can be formed from a contiguous element forming the entire wave pattern (typically with one joint connecting two ends of an elongated member), or from a number of interconnected segments, together forming the wave pattern.

The wire and/or filaments can be made from any biologically compatible resilient material. For example, the material can be a metal, an alloy, a plastic, and combinations of these materials. In some embodiments, the material is a spring metal, such as stainless steel. In other embodiments, the material is an alloy. Preferably, the alloy is a superelastic alloy capable of withstanding the application of large forces and large movements and being able to recover from such large strains.

Figure 2B:
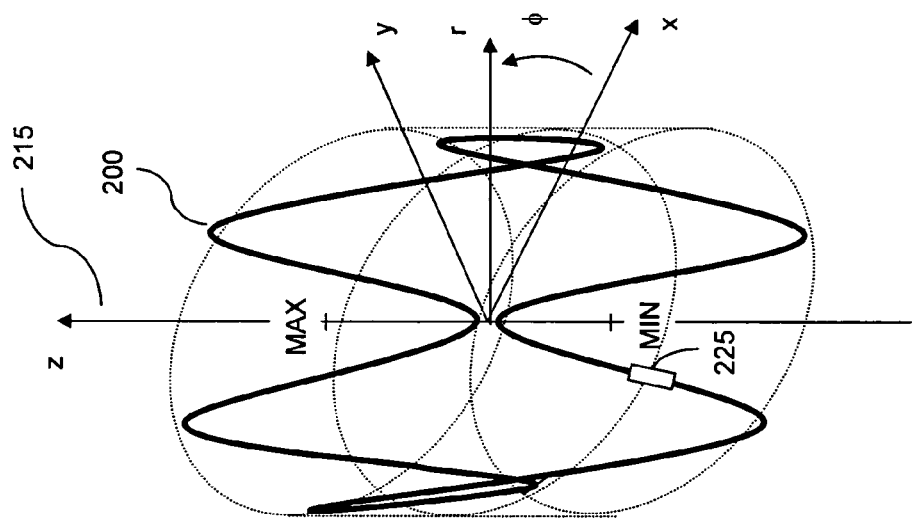
FIG. 2B is a schematic diagram of a perspective view of an alternative embodiment of the invention.

One example of a superelastic alloy is Nickel-Titanium (NiTi) compound commonly referred to as Nitinol. In one particular embodiment, the wave anchor 200 is made from a single Nitinol wire having a diameter from about 0.012 inches to about 0.020 inches. As the dilation force may not be sufficient to securely fasten the device to the local anatomy, some embodiments include anchoring features. For example, referring to FIG. 2B, a number of anchors 250 are coupled to the wave anchor 200. Thus, the ability of the wave anchor is to remain securely fastened to the body is enhanced by the addition of hooks and/or barbs 225.

Figure 3A:
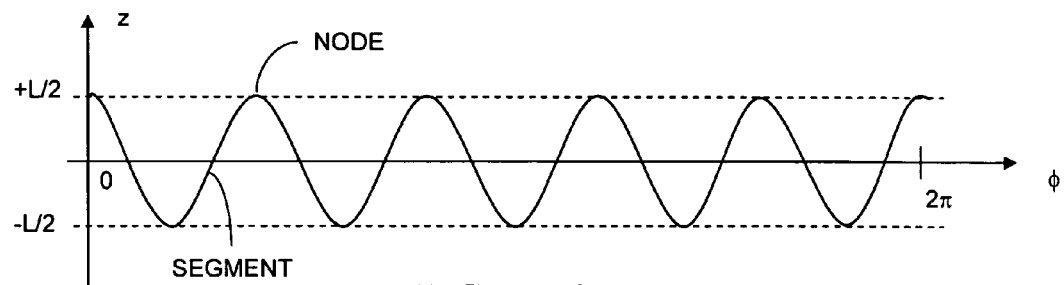
FIGS. 3A through 3D are schematic diagrams of exemplary alternative embodiments of a wave pattern.
Figure 3B:
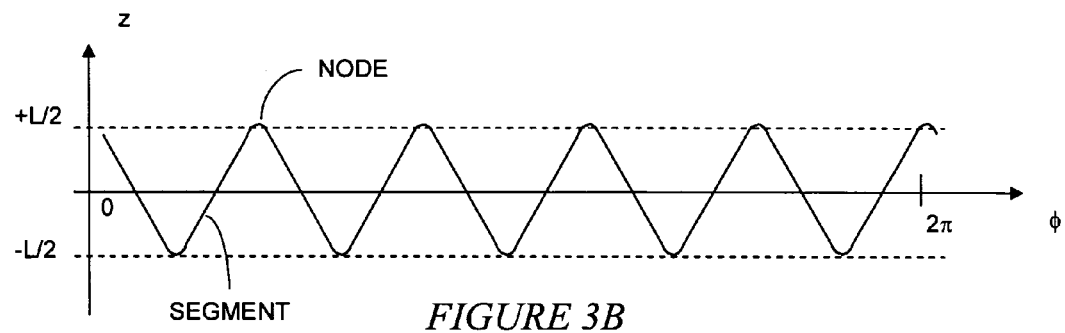
Figure 3C:
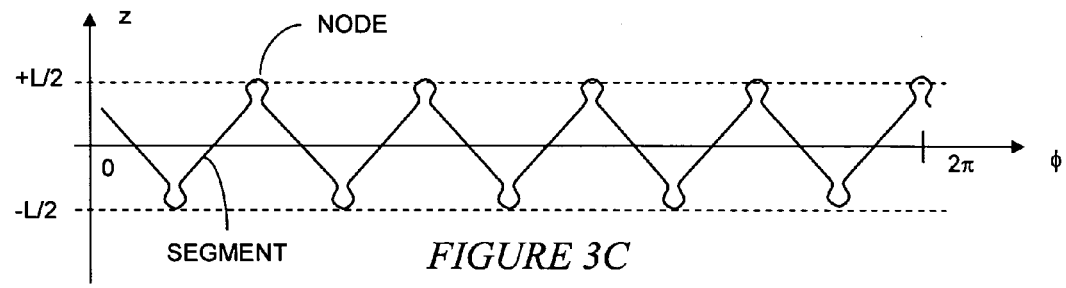
Figure 3D:
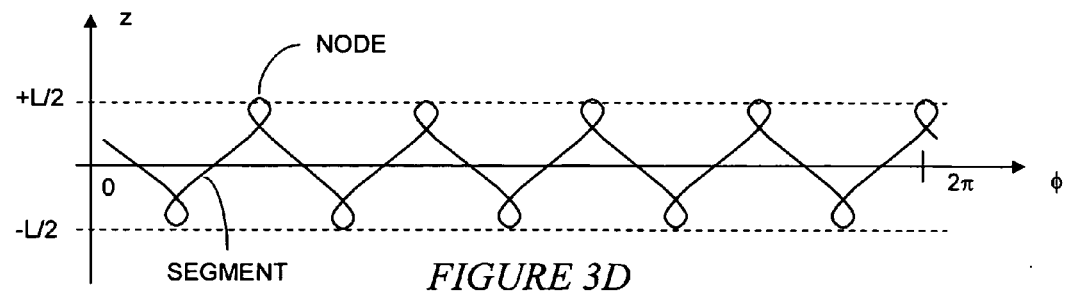

FIGS. 3A through 3D are schematic diagrams of exemplary alternative embodiments of a five-node wave pattern. In FIG. 3A, the wave pattern is sinusoidal, extending along the z-axis between a maximum value of one-half of the device length (i.e., +L/2) to a minimum value of minus one half of the length (i.e., −L/2). As indicated, the pattern is traced over a radial distance of $2\pi$ radians along an imaginary cylinder having a radius equal to half the diameter of the device (i.e., D/2). FIG. 3B illustrates an oscillating pattern formed by linear segments of alternating pitch in which adjacent segments are joined together at their ends by a curved segment. FIG. 3C illustrates a similar oscillating pattern formed by adjacent linear segments of alternating pitch in which adjacent segments are joined together at their ends by exaggerated curved segments. Such exaggerated curved segments can reduce the stresses experienced at the ends of the device, thereby reducing the chances of material fatigue. Finally, referring to FIG. 3D, one embodiment of the device includes a number of substantially linear segments of alternating pitch in which adjacent segments are joined together using a loop. The loop can be formed by bending the elongated member beyond $\pi$ radians at the each of the nodes.

Advantageously, an anchor device formed from a wire is simple to manufacture. For example, the device can be formed from a single Nitinol wire fashioned into any of the annular waves shown in FIGS. 2 and 3. The two ends of the wire can be joined, or otherwise secured together to form a continuous wire structure. For example, the ends of the wire can be joined together using a weld, a bond, a mechanical crimp, a constricting sleeve, and combinations thereof. Notably, the shape, selection of materials, and construction of the device allow it to be radially compressed by a substantial amount without losing its original shape and dimensions. For example, the device can accommodate a very large diameter $D_1$, such as the diameter of an adult human's intestine of up to about 45 mm, while advantageously allowing it to be radially compressed, or packed into a delivery system having a smaller diameter $D_2$ of 12 mm or less. Also, the radial force provided by the device can be controlled by the wire diameter from which it is made.

Figure 4:
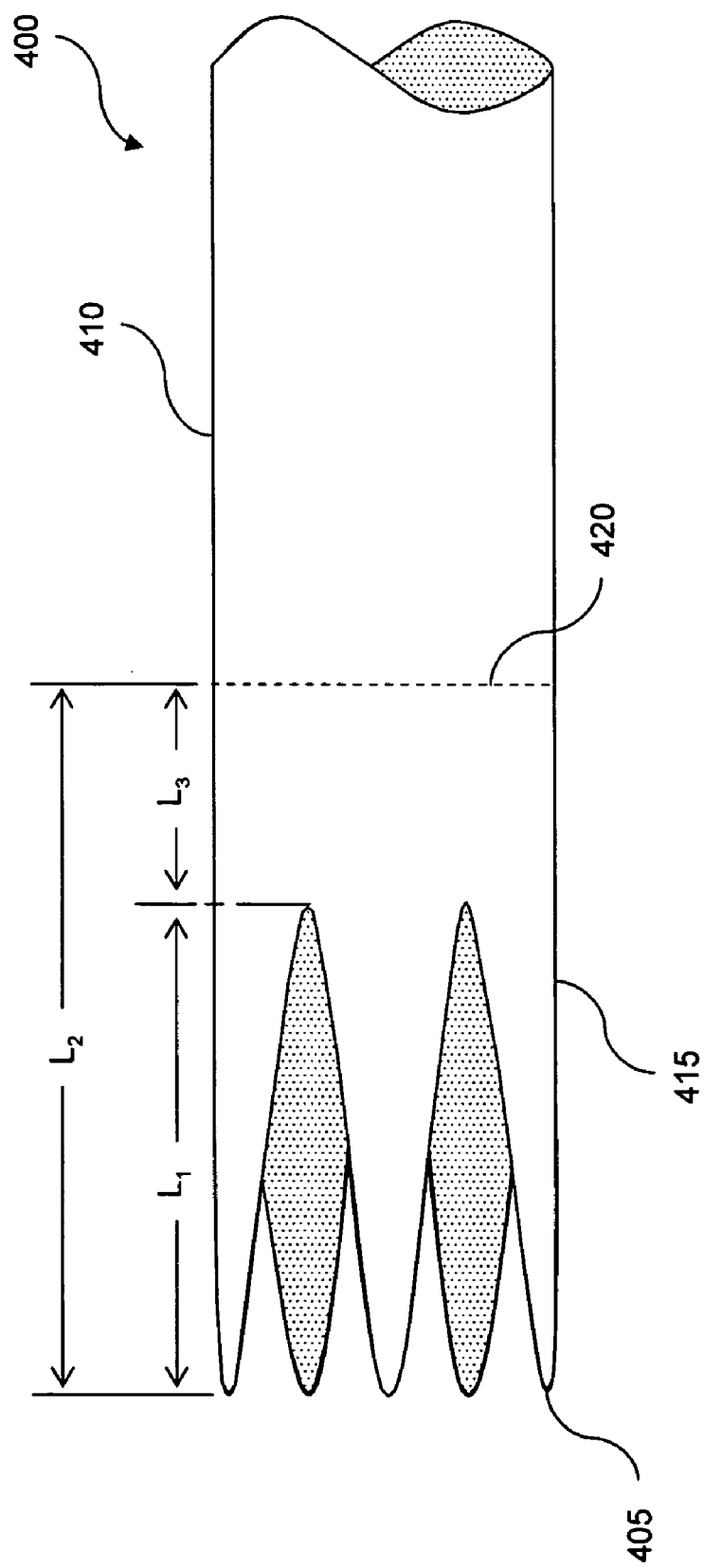
FIG. 4 is a schematic diagram of a side view of an embodiment of the invention including an elongated sleeve.

FIG. 4 is a schematic diagram of a side view of an embodiment of the invention in which an anchor is attached to a medical device. In the exemplary embodiment, the medical device is an elongated sleeve. As shown, the proximal end of the wave anchor 415 forms an annular ring having a wave-like shape formed about its perimeter. Preferably, the sleeve material proximal to the anchor 415 is cut back to match this shape of the anchor 415 (e.g., forming a "tulip" shaped end). Such a configuration facilitates the formation of a seal at the proximal end of the sleeve 400 and also allows for independent movement with flexure of the anchor 415. Thus, proximal ends of the different "petals of the tulip" can flex independently as the sleeve material 410 does not restrain them. Additionally, the tulip-shaped proximal end, when installed, forms a secure seal along its entire perimeter when implanted in the gastrointestinal tract. Advantageously, such a tailored fit leaves no unsupported material between the edges of the device that food can get behind.

Generally, the proximal end of a sleeve device 400 is configured for reversible anchoring within the body. Notably, however, the sleeve device 400 does not require significant dilation force, as it is not supporting an opening into which it is placed (i.e., it is not a stent). Thus, the sleeve device 400 includes at least one anchoring, or securing device 415, attached to the sleeve 410. The purpose of the proximal sleeve anchor 415 is primarily to hold the sleeve 100 in place. Additionally, the anchor 415 provides some radial force to ensure that the sleeve 410 provides a fluid seal against the local anatomy. Such a seal is particularly important for intestinal applications. In the intestine it is desirable to constrain the flow of chyme within the lumen of the sleeve device 400, reducing or eliminating the likelihood of chyme passing around the device. Beneficially, the propulsive force of the stomach acts to push chyme into the device 400, ensuring that most of the chyme will enter the device.

As shown, the anchor device 415 can be fastened to the sleeve 410 at its proximal end. The material can be attached to the anchor 415 by mechanical and/or chemical bonding, welding, and/or using other mechanical fasteners including sutures. In some embodiments the anchor 415 is attached to the sleeve 410 by sandwiching it between an inner and outer layer of the sleeve 410. Thus, in some embodiments, the material of the sleeve 410 extends around the radial exterior of the anchor device 415. In this manner, the material can be folded back to a length $L_2$ measured from the proximal end of the device 400. Generally, the length $L_2$ is greater than the axial extent of the anchor 415, $L_1$. Advantageously, the double layer of material 410 extends a distance L3 measured in a distal direction from the distal end of the anchor 415. The overlapping material 410 can be fastened together near the end of the overlap 420. For example, the two layers can be stitched together along the line 420. Alternatively, the two layers can be chemically or thermally bonded together along the same line 420.

Generally, the sleeve is unsupported, having material properties selected to minimally irritate, or otherwise affect normal operation of the intestine. Thus, the material 410 is thin, light weight, supple and biocompatible. For example, the sleeve 410 can be formed from an elastomeric material such as urethane and/or silicone rubber. Alternatively, the sleeve 410 can be formed from a substantially non-elastomeric material, such as a fluoropolymer and/or polyolefin. Some examples of fluoropolymers include PolyteTraFluoroEthylene (PTFE), expanded PTFE (ePTFE), Fluorinated Ethylene Propylene (FEP), PerFluoroAlkoxy (PFA), Ethylene TetraFluoroEthylene (ETFE), and PolyVinyliDene Fluoride (PVDF). Some examples of polyolefins include polyethylene and polypropylene. The intestinal sleeve 410 is preferably thin-walled, unsupported and made of a flexible material that can be collapsed with minimal pressure from the outside. Thus, the unsupported, thin-walled material is naturally in a collapsed state and is opened only by pressure formed within the lumen of the sleeve 410. In some embodiments, the thickness of the sleeve material is less than about 0.001 inch. The sleeve is preferably formed from a low friction material having a coefficient of friction of less than about 0.3. More preferably, the coefficient of friction is less than about 0.2. A low coefficient of friction facilitates insertion of the sleeve 410 within a body, and further facilitates passage of chyme therethrough.

Notably, as there is no network of struts with this design, the only substantial force on the surrounding tissue is along the outer surface area of the wire itself. For example, a five-node sinusoidal wave anchor having a length $L_1$ of 1 inch, and a diameter $D_1$ of about 1.8 inches formed from a 0.016 inches diameter wire provides a surface area of about 0.224 square inches. This results in a dramatic reduction in the surface area of the tissue in contact with or otherwise affected by the anchor 415 (i.e., only the tissue in contact with the wire anchor), compared to typical, stent-type devices. It is therefore very unlikely that the ampulla of Vater 124, which empties into the duodenum, would be blocked by this anchor when implanted within the upper intestine in the vicinity of the ampulla of Vater 124, even though the sleeve 410 extends across and beyond the ampulla of Vater 124. Longer and more stent-like devices would be more likely to lie over the ampulla of Vater 124 potentially blocking it. More generally, the sleeve can be anchored at other locations within the gastrointestinal tract. For example, the anchor can be placed in the stomach with the sleeve extending into the intestine. Alternatively or in addition the sleeve can be anchored in the duodenum below the ampulla of Vater 124, or even in more distal portions of the intestine, such as the jejunum or ileum.

Such light-weight material is prone to reflux in the proximal direction. In some instances, the reflux results in a part of the material 410 extending beyond the proximal end of the anchor 415. This situation is generally undesirable resulting from back pressure originating in the distal intestine. Beneficially, the overlap described above provides additional strain relief at the proximal end of the sleeve 410 to resist such reflux.

Figure 5A:
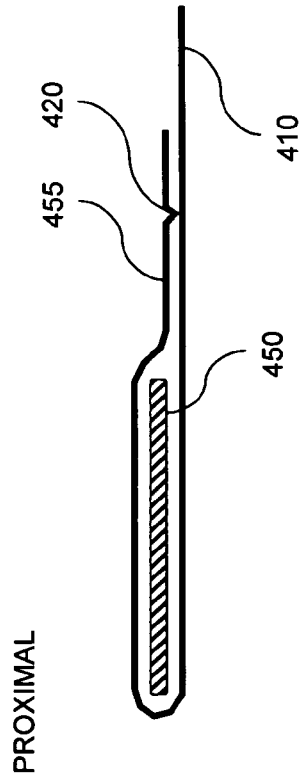
FIGS. 5A-5C are schematic diagrams showing alternative types of reinforcement of the embodiment of the invention shown in FIG. 4.
Figure 5B:
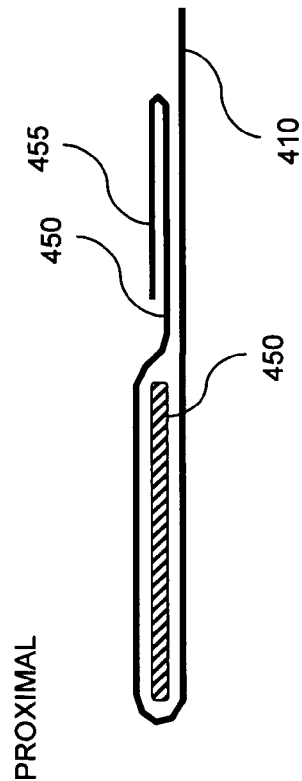
Figure 5C:
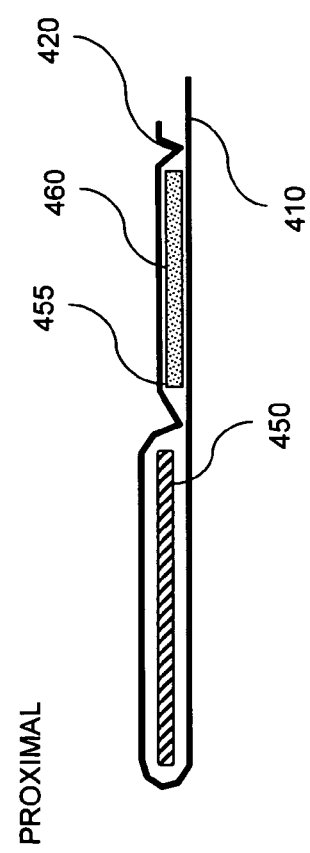

A cross-section of a portion of the proximal end of an unsupported sleeve including a proximal anchor is shown in FIGS. 5A-5C. The proximal anchor 450 can be sandwiched between two layers of the sleeve material 410. As shown, the proximal end of the sleeve 410 can be folded back upon itself, substantially enclosing the anchor 450 therein. An extended double layer of the sleeve 455 can be continued for a predetermined length extending distally from the distal end of the anchor 450. Such a double layer can provide additional strain relief. To secure the sleeve configuration, the two layers 410, 455 can be attached together. For example, the layers 410, 455 can be attached using sutures, staples, and/or chemical or thermal bonding 420. In an alternative embodiment shown in FIG. 5B, the sleeve 410 can be folded forming more than two layers 455, thus providing even greater support and rigidity than the double layer. Still further, the sleeve 410 can be folded about a supporting member 460.

Figure 6:
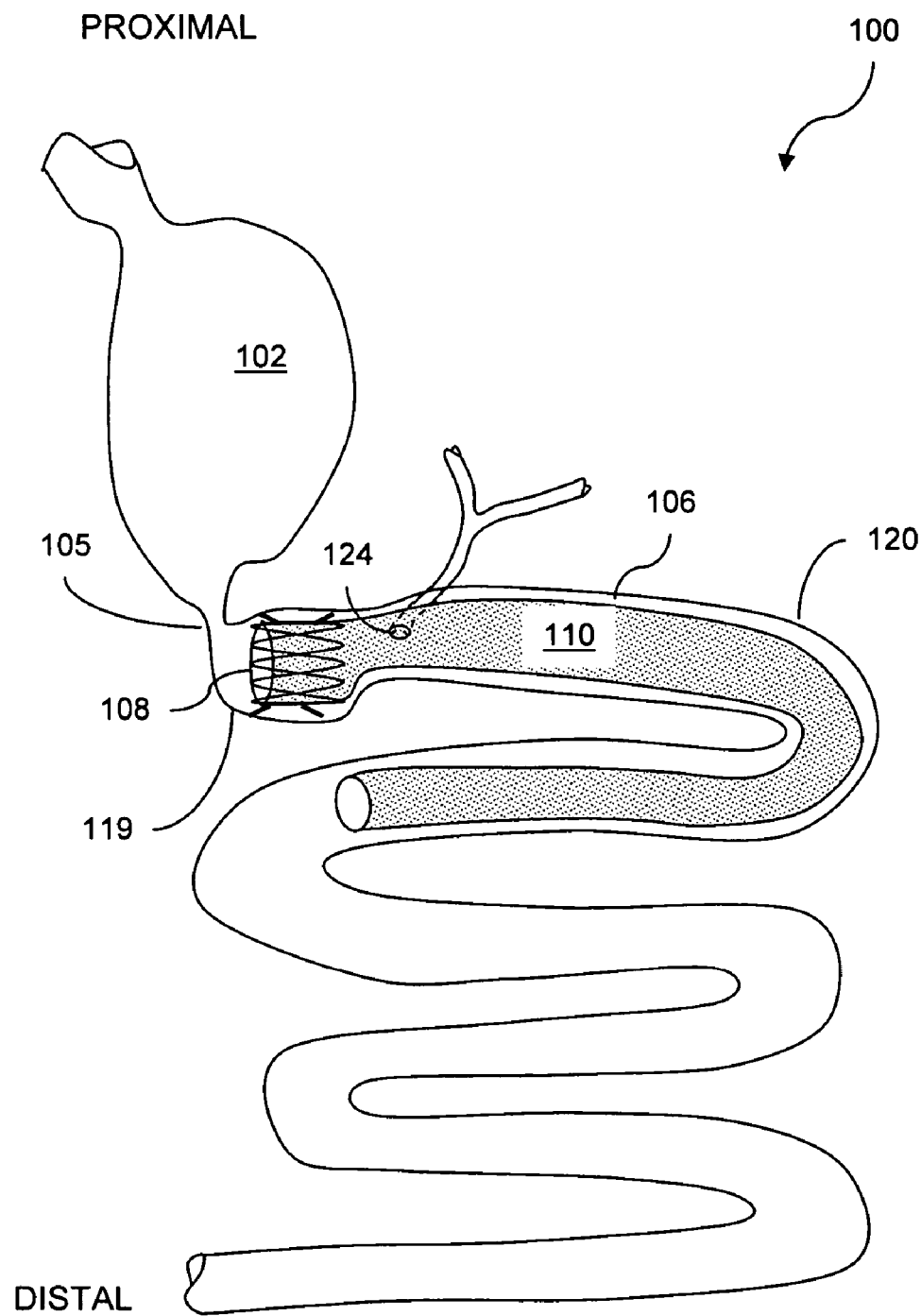
FIG. 6 is a schematic diagram of an embodiment of the invention illustrated in FIG. 4 implanted within a natural lumen of a gastrointestinal tract of an animal body.

Referring now to FIG. 6, one embodiment of the invention is shown implanted within a natural lumen of a gastrointestinal tract of an animal body. In the exemplary implantation, an anchor 108 anchors an unsupported flexible sleeve 110 within the duodenum 106. In particular, the anchor is placed within the duodenal bulb 119, which is located just distal to a pylorus 105. At least one advantage to anchoring in the duodenal bulb 119 is that there is relatively less motion compared to other parts of the duodenum 106. Further, the motion in the duodenal bulb 119 tends to be limited contractions, rather than contractions and linear movements. Still further, the surrounding muscular tissue of the duodenal bulb 119 is relatively thick, thinning as one moves away from the pylorus 105, facilitating attachment of the anchor 108. The thick tissue is particularly advantageous in anchors using barbs.

Figure 7:
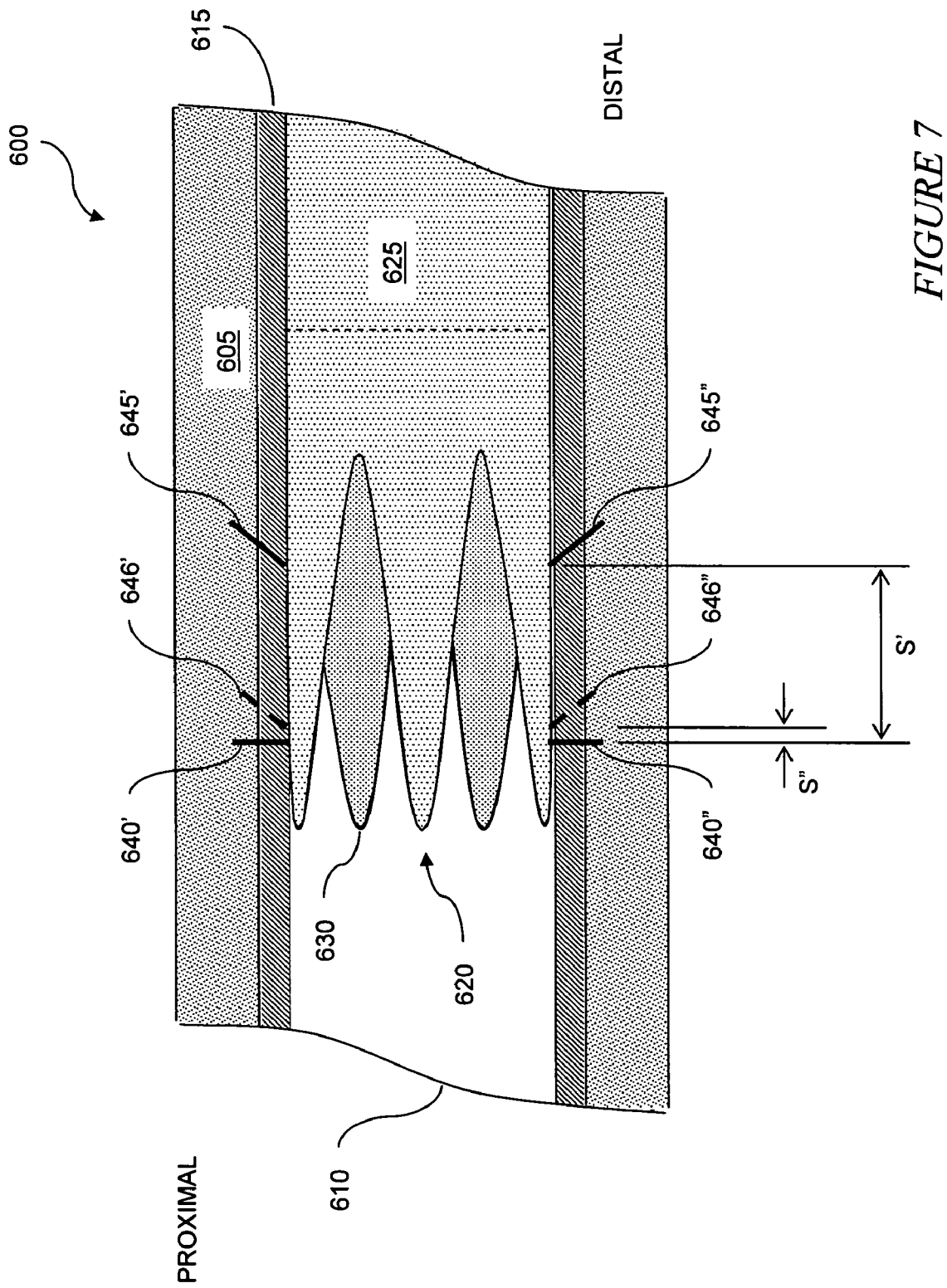
FIG. 7 is a more-detailed cross-sectional diagram of one embodiment of the invention inserted within a natural lumen.

At least one advantage resulting from anchoring at the duodenal bulb 106 is that the pylorus 105 is allowed to open and close normally. As described above, the length of the anchor 108 is minimal to ensure that the ampulla of Vater 124 is not blocked. This distance in an average adult human between the pylorus 105 and the ampulla of Vater 124 is at least about 2 inches. Thus, the length of the anchor 108 is preferably less than about 2 inches. Additionally, as described above a flare can be provided at the proximal end of the anchor 108 functioning as a stop against the distal side of the pylorus 105 to resist reflux of the device 110 into the stomach 102. The flare also helps direct chyme flowing from the stomach 102 into the center of the anchor 108 and sleeve 110. Still further, the flare helps reinforce engagement of any proximally-located barbs with the surrounding tissue FIG. 7 is a more-detailed cross-sectional diagram of one embodiment of the invention inserted within a natural lumen. Generally, the natural lumen 610 is formed within the interior of a hollow organ, such as the intestine 600. The cross-section of the intestine 600 includes a number of different layers. For example, the intestine 600 includes muscular layer 605 including muscular tissue for aiding in the passage of food. Additionally, the intestine includes a mucosal layer 615 along the interior surface of the lumen. In the intestine, the mucosal layer 615 is a mucosa layer formed of loose tissue. A gastrointestinal implant 620, similar to the one shown in FIG. 4 is shown secured within the intestine 600. Thus the gastrointestinal implant 620 includes a wave anchor 630 coupled to the proximal end of an elongated sleeve 625. The proximal end of the gastrointestinal implant 620 includes a number of barbs arranged in at least two layers: a proximal layer of barbs 640', 640" (generally 640) located near the proximal end of the anchor 630; and a distal layer of barbs 645', 645" (generally 645). In some embodiments, the distal barbs 645 are located near the distal end of the anchor 630. In other embodiments, distal barbs 646', 646" (generally 646) are located closer to the proximal end of the anchor 630 and can even be just distal to the proximal barbs 640. As shown, the barbs 640, 645 preferably penetrate the mucosa layer 615 extending into but not through the muscular layer 605.

Figure 8A:
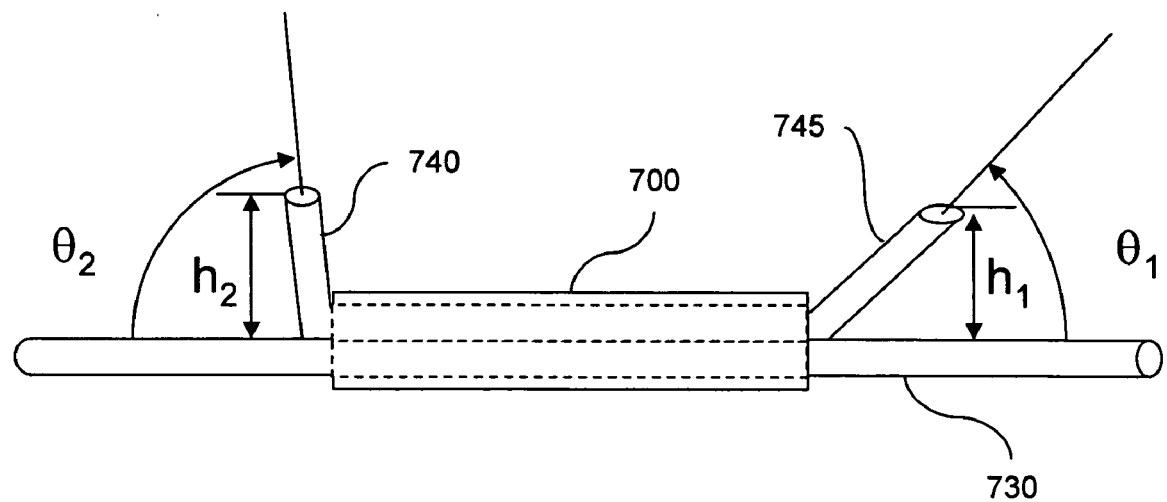
FIG. 8A is a more detailed schematic diagram of an embodiment of the barbs illustrated in FIG. 7.

In more detail, referring now to FIG. 8A, barbs 740, 745 can be attached directly to the wave anchor 730. For example, one or more barbs 740, 745 can be fastened to one or more of the legs or struts 730 of the wave anchor. The barbs 740, 745 can be fastened to the struts 730 by welding, bonding, or crimping means. Additionally, the barbs 740, 745 can be fastened to the struts 730 using a mechanical fastener, such as a clasp or splice 700. In some embodiments, the barbs 740, 745 can be formed contiguous with the struts 730. Alternatively, or in addition, the barbs 740, 745 can be molded onto the struts 730. For example, barbs can be formed by injection molding a first material onto the supporting struts 730. The barbs can be injection molded onto a completely formed anchor 730, and/or injection molded onto a substrate, such as a wire, that is later formed into the anchor 730. Such injection molding techniques are well adapted to forming erodible barbs of a first material upon the supporting anchor 730 formed from a second material, such as stainless steel or Nitinol. For example, the erodible barbs can be formed from PolyLActide (PLA), PolyGlycolic Acid (PGA), and/or PolyparaDioxanone (PDS). Advantageously, depending on the configuration of the erodible materials, they can be formed to erode after a predetermined period of implantation. In some embodiments, a large number of barbs 740, 745 (e.g., 80 barbs) are provided around the wave anchor.

In some embodiments, the barbs 740, 745 reside within a plane containing the central axis of the anchor 730. Thus, the barbs extend outward containing an axial component and a radial component, but not a transverse component. Alternatively, the barbs can extend outward from the central axis in a direction having a transverse component. For example, the barbs could reside substantially in a plane perpendicular to the central axis. Barbs having a transverse component can prohibit twisting of the anchor about its central axis.

The barbs 740, 745 can be fabricated from a shape-memory material, or a superelastic material. For example the barbs can be formed from a Nitinol wire having a diameter between about 0.016-0.025 inches. The barbs 740, 745 can also be formed from a rigid, yet resilient material such as stainless steel. Preferably, the barbs 740, 745 are designed to penetrate into the surrounding intestine wall, but not through it. Accordingly, the length of the exposed barb 740, 745 is controlled depending on the application. For example, for placement within the upper intestine, the barbs 740, 745 are approximately 3 mm long and extend outward from the device at an angle of about 45 degrees to a height (i.e., penetration depth) of about 2 mm. This ensures that the barbs 740, 745 penetrate the mucosa layer of the intestine and attach to the underlying tissue.

The angle of each of the barbs 740, 745 can also be varied depending on the desired effect. In some embodiments, proximal barbs 740 extend from the anchoring device 630 in a proximal direction; whereas, distal barbs 745 extend from the anchoring device 630 in a distal direction. An angle is defined between the axis of each barb 740, 745 and the surface of the wave anchor. In some embodiments the distal barbs 745 form a first angle $\theta_1$, while the proximal barbs 740 define a second angle, $\theta_2$. In some embodiments, the first angle is a shallow angle, such as $\theta_1 = 10$ degrees, while the second angle is substantially steeper (e.g., closer to 90 degrees). In other embodiments, both angles are about 45 degrees. In addition to the angle, the barb heights $h_1$, $h_2$ control the respective depths of penetration into the surrounding tissue. For example for intestinal applications, a height of about 2 mm is preferred to penetrate into the muscular layer of the intestine without necessarily puncturing the outer surface of the intestine.

Figure 8B:
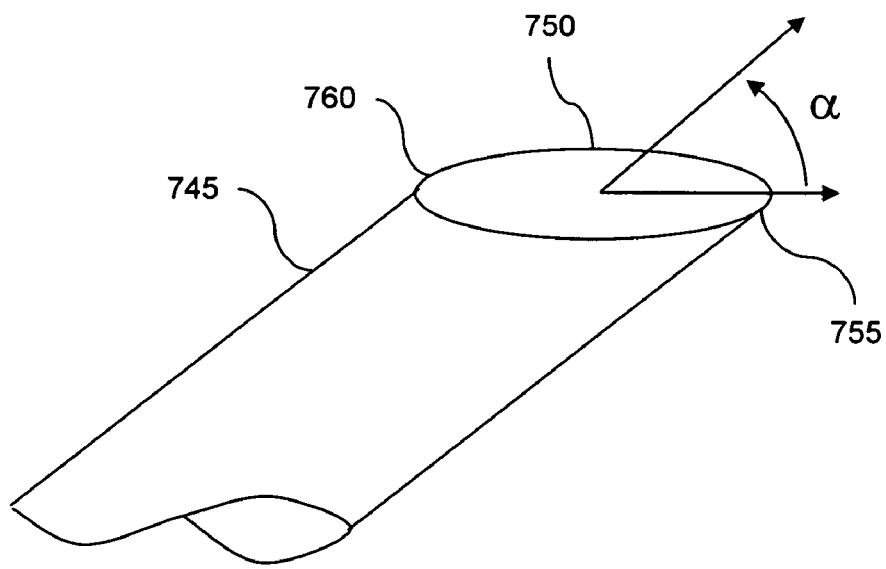
FIG. 8B is a more detailed schematic diagram of the tip of one of the barbs illustrated in FIG. 8A.

A more detailed schematic diagram of the tip of one of the distal barbs 745 is illustrated in FIG. 8B. Notably, the end surface of the barb 745 can be fashioned with a predetermined profile. For example, the tip of the barb 760 can be blunt, tapered, and/or pointed. Additionally, the tip of the barb 760 can be directionally pointed, as shown. Thus, an angle formed between the axis of the barb 745 and its end surface area $\alpha$ is selected to provide a sharp profile along its leading edge 755 and a blunt profile along its trailing edge 760. Thus, movement of the distal barb 745 in a proximal direction will not pierce the surface of the natural lumen; whereas, movement in a distal direction will result in the leading edge 755 tending to pierce the tissue of the natural lumen. Such a directional profile can aid in implanting the device at a desired location. That is, the device can first be placed distal to the desired location, then drawn proximally to the desired location and finally pushed distally again to set the distal barbs 745 into the tissue.

Figure 8C:
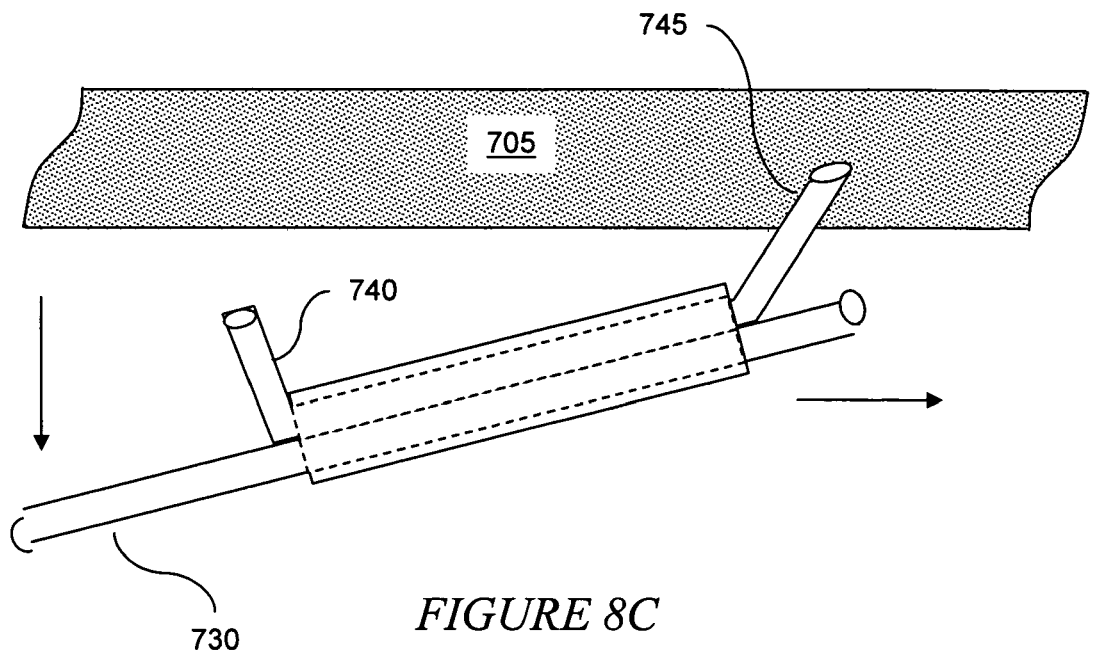
FIGS. 8C-8D are schematic diagrams of insertion of the embodiment of the invention illustrated in FIGS. 8A and 8B within a natural lumen.
Figure 8D:
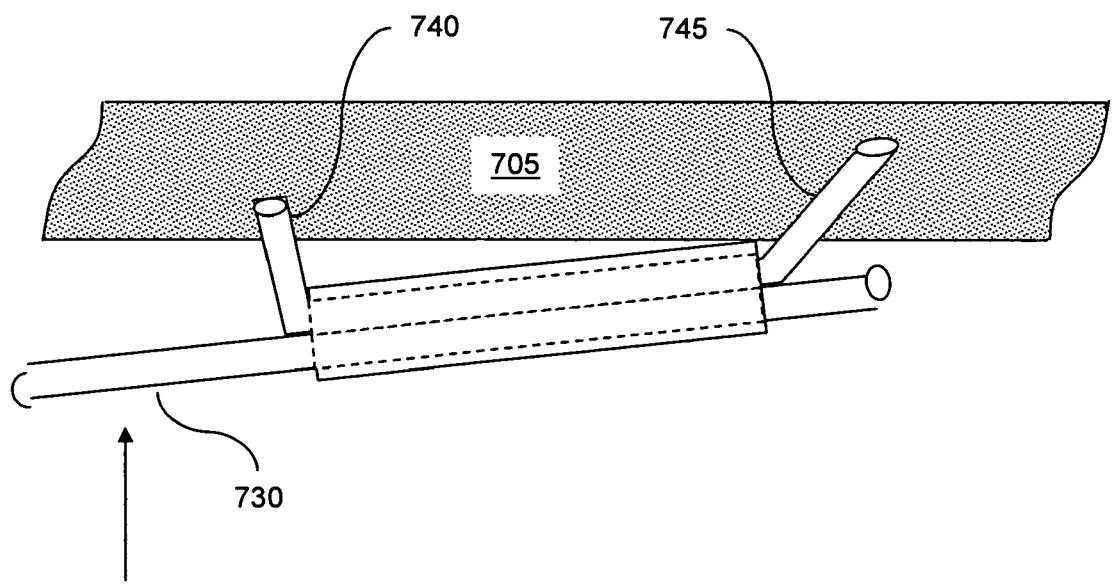

FIGS. 8C-8D are schematic diagrams of one the embodiment of the invention being inserted within a natural lumen. Generally, during implantation, the distal barbs are set first. The compressed device is inserted into a predetermined location with the lumen and the distal end of the anchor is released allowing the distal barbs to come into contact with the tissue of the lumen. Then, as described above, distal movement of the device along the axis of the lumen causes the distal barb 745 to insert itself into the tissue 750. Once set, the proximal end of the anchor is released from its compressed state allowing the proximal barbs to pierce into the surrounding tissue 750. As the movement of the barb is substantially perpendicular to the surface of the lumen, the high angle results in the barb approaching the surface tissue at a substantially perpendicular angle. Once implanted, the barbs 740, 745 operate to secure the device to the surrounding tissue 750 resisting axial movement along the lumen, and also securing the anchor during radial expansion of the lumen.

To remove the anchoring device, it can be grasped at its proximal end and collapsed radially. Further, the radially collapsed anchoring device itself can be drawn into a sleeve or catheter for removal. Thus, the proximal barbs 740 being more vertical are easier to remove from the tissue 750 as the proximal end of the device is radially collapsed. Once the proximal end is collapsed, the device can be pulled proximally allowing the distal barbs 745 to slide out of the tissue 750 due to their lower angle. In some embodiments, the proximal and distal barbs 740, 745 are formed having substantially the same angle.

Figure 8E:
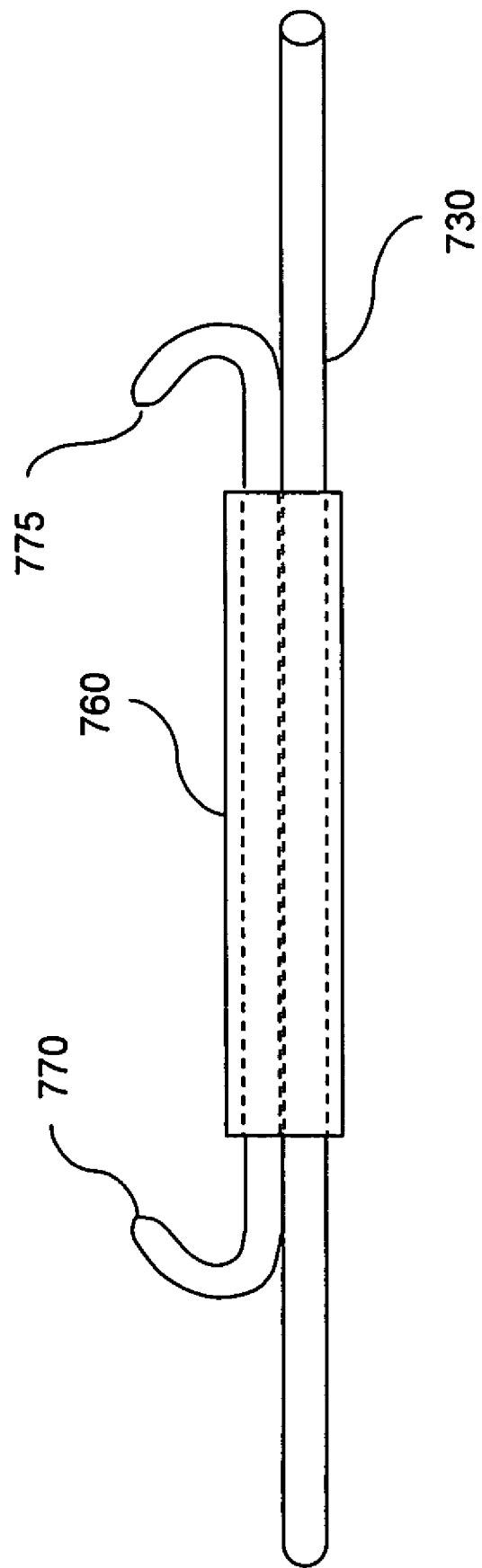
FIG. 8E is a schematic diagram of an alternative embodiment of barbs.

In some embodiments, the barbs include hooks 770, 775 to grasp the tissue of the surrounding anatomy, such as those shown in FIG. 8E. The hooks 770, 775 can be attached to one or more legs 730 of the anchor. For example, the hooks 770, 775 can be welded, bonded, or crimped to one or more of the legs 730 of the device. As shown, the hooks 770, 775 can be formed from a single filament of wire attached to one of the legs 730 using a crimp sleeve 760. Thus, different materials can be used for hooks 770, 775 and the anchor itself. Alternatively, the hooks can be formed from different material, with each hook independently being attached to the leg 730.

In some embodiments, the hooks 770, 775 are fabricated from a shaped-memory material, such as Nitinol wire. Preferably, the shaped-memory alloy is set for phase transition at around body temperature. Thus, the hooks 770, 775 can be cooled before insertion and configured in a substantially straight configuration to pierce the tissue of the surrounding anatomy. Then, when inserted into the tissue, a resulting raise in temperature to body temperature leads to a phase transition resulting in the hooks 770, 775 re-shaping into hook-shape to grasp the tissue. For removal, the anatomy in the region of the hooks 770, 775 can be cooled below body temperature, and below the phase-transition temperature to again straighten the hooks 770, 775 thereby facilitating removal from the tissue. For example, the hooks 770, 775 can be cooled with cold-water injection to soften the hooks 770, 775 for installation and also for removal from the body. The hooks 770, 775 can also be Nitinol, superelastic wires that are flattened during delivery and when released, they spring into the tissues.

If shape memory, they lay flat at room temperature to be collapsed for easy insertion into the body. The hooks take shape at body temperature to anchor into the tissue. If superelastic, they are forced flat and placed in a tube for loading and the anchors spring to shape as they are pushed out of the delivery tube. FIG. 4C illustrates pre-deployed barbs. FIG. 4D illustrates deployed barbs and FIG. 4E illustrates the collapsed system for delivery.

Figure 9:
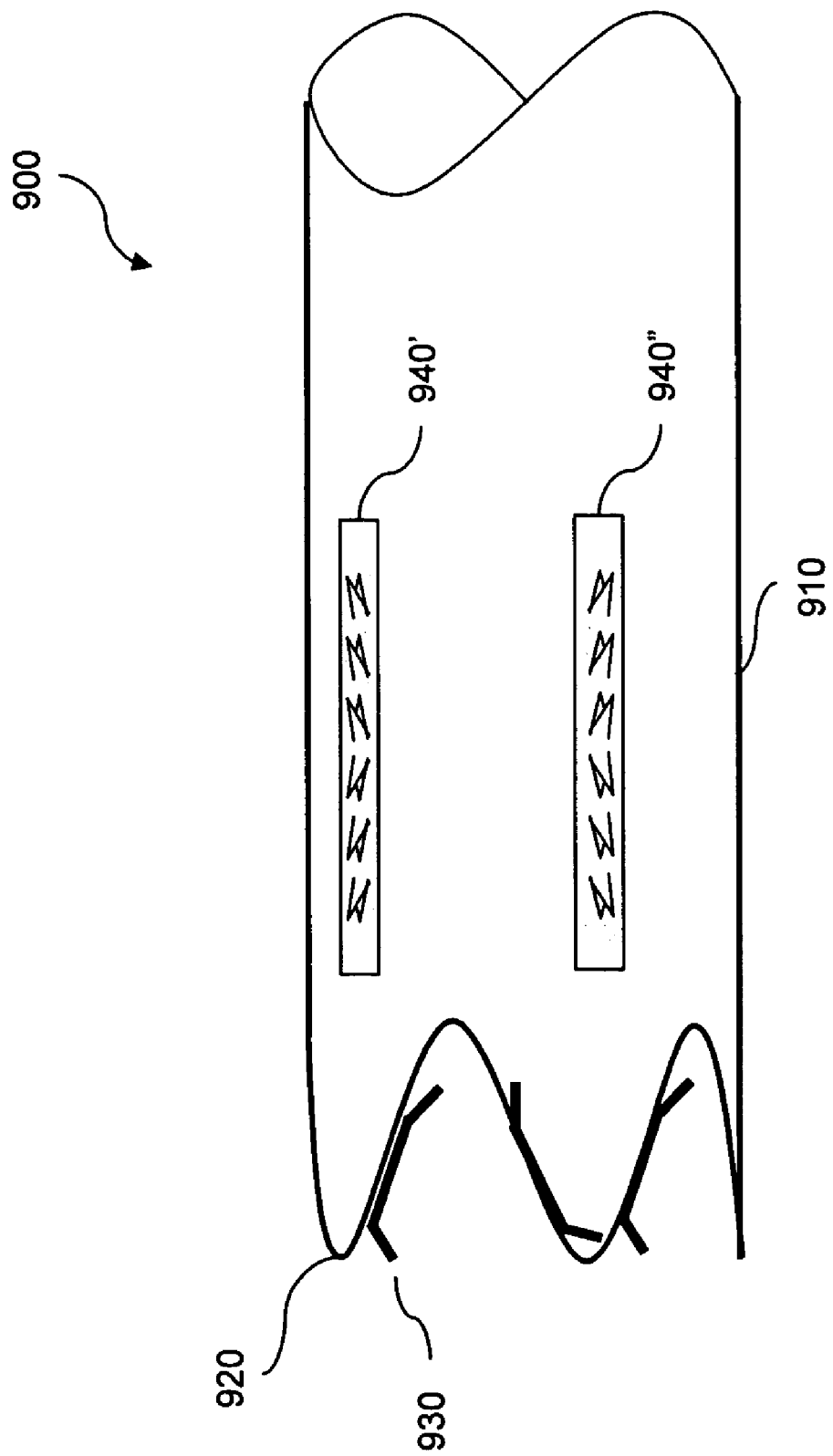
FIG. 9 is a schematic diagram of a side view of an alternative embodiment of the invention including sleeve barbs.

FIG. 9 is a schematic diagram of a side view of an alternative embodiment of the invention 900 including a wave anchor 920 coupled to the proximal end of an elongated sleeve 910. In some embodiments securing devices 940', 940" are provided on the sleeve 910, not necessarily at its proximal anchor 920. For example, as shown in FIG. 9, a sleeve device 900 includes a flexible sleeve 910 having a first anchoring device 920, such as a wave anchor, at its proximal end. In some embodiments, the wave anchor 920 can maintain its position within the gastrointestinal tract by relying on its radial force exerted upon the surrounding tissue. Alternatively, the wave anchor 920 can include one or more anchoring elements, such as a number of barbs 930 similar to those described above in relation to FIGS. 8A-8E, to further secure the proximal end of the device 900.

Additional anchoring elements 940', 940" can be positioned along the flexible sleeve 910, separate from the wave anchor 920. For example, anchoring strips 940', 940" (generally 940) can be attached to the sleeve 910. Each anchoring strip includes one or more barbs. For example, a strip 940 can include multiple barbs linearly arranged along the strip 940.

Figure 10A:
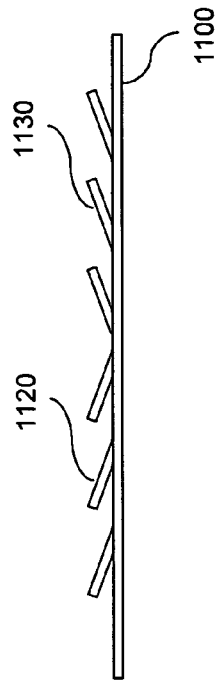
FIGS. 10A-10B are more detailed schematic diagrams of one embodiment of sleeve barbs.
Figure 10B:
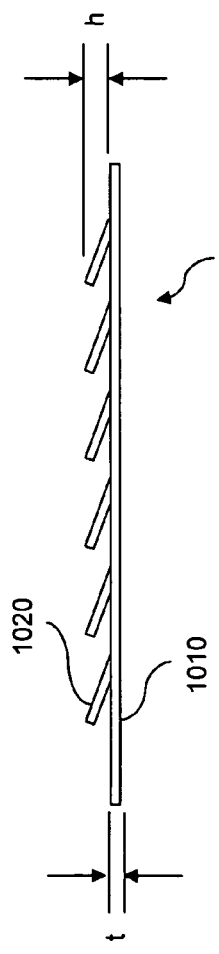

FIGS. 10A-10B are more detailed schematic diagrams of one embodiment of sleeve barbs 940. An anchoring strip 1000 includes a mounting frame 1010 and a number of barbs 1020, each of the barbs 1020 coupled at one end to the frame 1010. Preferably, the strip 1000 is compliant and flexible. For example, the strip 1000 can be formed from a thin strip of shape memory material, such as Nitinol, or stainless steel, having a thickness 't' selected to ensure the desired flexibility. In some embodiments, the barbs 1020 can be attached to the mounting frame 1000 by mechanical fasteners, welding, and/or chemical bonding. In other embodiments, the barbs 1020 can be formed from the material of the strip 1000. For example, the barbs can be formed by cutting a shape, such as a triangle into strip 1000, then bending the triangles outward from the strip, such that the barbs 1020 will engage the surrounding tissue when implanted. To ensure that the anchoring strip 1000 is flexible, the width of the strip '$W_1$', including the width measured from the edge of the strip 1010 to the edge of the barb '$W_2$' is controlled to a minimum distance.

In some embodiments, all of the barbs 1020 of a strip 1000 are oriented in the same direction to prevent movement in a one direction. In this manner multiple anchoring elements 1000 can be mounted to a single sleeve 910, with all of the anchoring elements 1000 providing barbs 1020 substantially aligned in the same direction. Alternatively, the orientations of the multiple anchoring elements 1000 can be varied, such that some barbs 1020 are aligned in one direction, while other barbs 1020 are aligned in another direction. In other embodiments, the barbs are formed substantially perpendicular to the surface of the strip 1010 to prevent motion in either direction.

Figure 11A:
FIGS. 11A-11B are more detailed schematic diagrams of an alternative embodiment of sleeve barbs.
Figure 11B:
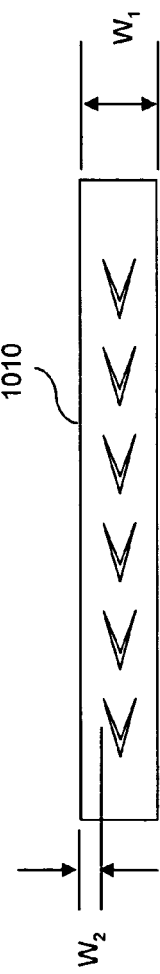

Alternatively, the barbs can be formed with different orientations on the same strip as shown in FIGS. 11A and 11B. Thus, an anchoring device 1100 includes a mounting strip 1110 containing a first barb 1120 oriented in a first direction and a second barb 1130 oriented in a different (e.g., opposing) direction.

In other embodiments, as shown in FIGS. 12A and 12B, an anchoring strip 1200 can be formed having a mounting strip 1210 formed from a moldable material, such as a polymer. In this manner, one or more barbs 1220 can be attached to the mounting strip 1210 by including a portion that is anchored within the strip 1210 itself. For example, as illustrated, the barbs 1220 can be formed from a segment of wire, such that a first portion of the wire segment is embedded within the mounting strip 1210, while a second portion of the wire segment protrudes from the mounting strip 1210, being adapted to engage the surrounding tissue when implanted.

Figure 13:
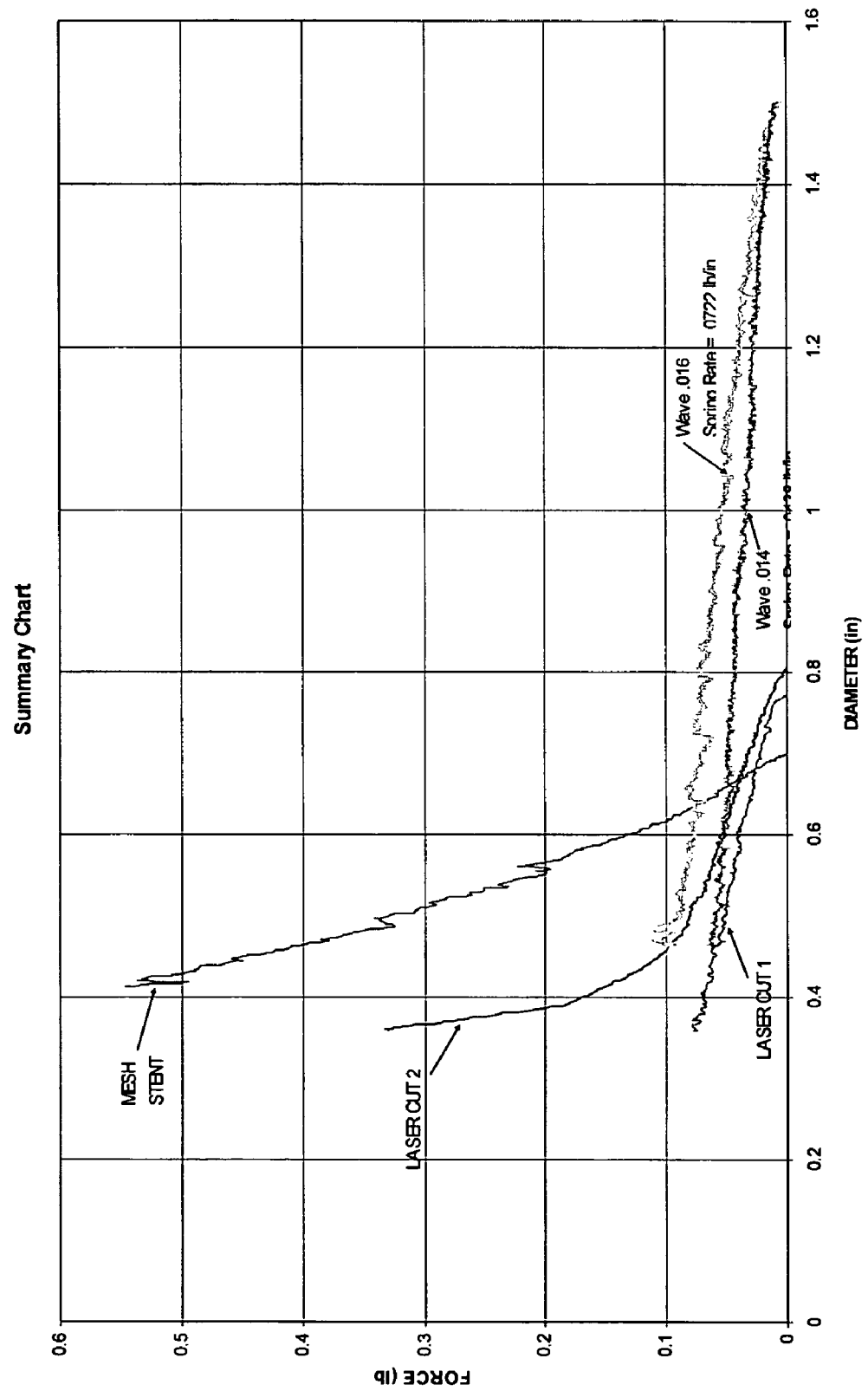
FIG. 13 is a graph of representative compliance curves for different embodiments of the invention.

An advantage of the wave design is the ability to form an anchor having a very flat compliance curve over a very long range of diameters. In general, referring now to FIG. 13, exemplary compliance curves show the radial force exerted by different devices as they are radially compressed. This means that the force against the tissue is substantially constant, even as the intestine contracts. Such a compliant device is less traumatic to the surrounding tissues. Exemplary spring rates of the above-described wave anchors are an order of magnitude less than mesh-type stents. Additionally, the resulting spring rates of the wave anchors are about half that of a typical Nitinol stent made from tubing. Further, the range of motion of commercial stents is less than about 0.5 inches whereas the wave anchors can operate in a range of up to about 1.5 inches with a substantially flat compliance curve. Exemplary test results are provided in Table 1 for known stent and for a number of other devices including wave anchors.

TABLE 1

Test Results

| | Mesh-type Stent | Wave-0.014 | Wave-0.016 | Laser-cut 1 | Laser-cut 2 |
|---|---|---|---|---|---|
| Spring Rate (lbs./inch): | 1.714 | 0.0438 | 0.0722 | 0.168 (long) 0.240 (short) | 0.253 |
| Approx. Range (inches): | 0.3 | 1.0 | 1.0 | 0.5 | 0.35 |

Depending upon the application, it may be necessary at times to periodically remove the medical device (e.g., sleeve) from the body. For example, an intestinal sleeve may be periodically removed to provide a rest period from material contact with the intestine, to adjust the therapy with a longer or shorter sleeve, and/or to replace the sleeve material before its useful life is over. Additional means to facilitate insertion, removal, and reinsertion, a two-part anchor includes a first portion fixedly attached within the body and a second portion adapted to removably engage the first portion. Thus, the first portion or permanent anchor can be fixedly attached (i.e., implanted) within a patient. Thus, a permanent anchor can be fastened to the patient using mechanical and/or chemical fasteners. Additionally, the permanent anchor can be configured to promote tissue in-growth to secure it within the body.

A second fastener can then be used to removably engage a medical device to the permanent anchor. For example, the second fastener can include a clip 1405 as illustrated in FIGS. 14A and 14B. Such a design enables a medical practitioner to easily fasten (e.g., "click") the medical device into and/or out of its position. Additionally, should a device, such as an intestinal sleeve become obstructed, it would be advantageous to allow the sleeve to dislodge itself and pass through the patient thereby avoiding potentially catastrophic consequences. Accordingly, in some embodiments, the fastening means release when the linear forces acting upon it increase sufficiently above a threshold to avoid harming the surrounding tissue. Thus, the permanent anchor remains in place, while the fastening means are designed to break away at a predetermined force, such as about 2 lbs. Once the device breaks away, it can be withdrawn (e.g., through the esophagus), or can pass normally through the bowel, while the permanent anchor remains in place, ready to accept another device.

The clip, or clasp 1405 can be formed by a loop defined at least in part by a spring member 1410. The loop also includes an opening 1415 that can be expanded by flexing the spring member 1410. Preferably the opening 1415 is normally closed when the spring member 1410 is not being flexed. Thus, a feature of a mating device, such as the sleeve, can be inserted into the clasp 1405, thereby securing the sleeve to the permanent anchor 1400 as described above. For example, the proximal end of the sleeve can include or more loops 1420 such as loops formed by the nodes of a wave anchor. Upon removal, the one or more loops 1420 can be extracted from the clasp 1405 allowing the sleeve to be separated from the permanent anchor 1400 and removed from the body. The permanent anchor 1400 remains within the body and can be used again in a similar fashion. In an alternative embodiment, the removable device includes one or more clasps configured to engage a feature, such as a loop, of the permanent anchor 1400.

In an alternative embodiment of a two-piece anchor can be fastened together using a magnetic fastener. For example, a permanent anchor can be provided with one or more magnets. A second, removable anchor can be provided with corresponding magnetically-attracted features configured to attach to the one or more magnets of the permanent anchor. Thus, the permanent and removable anchors are removably coupled together via magnetic attraction. Alternatively, the removable anchor can be provided with one or more magnets and the permanent anchor provided with corresponding magnetically-attracted features, the two anchor removably coupled together via magnetic attraction. Still further, each of the permanent and removable anchors can be configured with both magnets and magnetically-attracted features configured to magnetically couple with corresponding features of the other anchor.

Figure 15A:
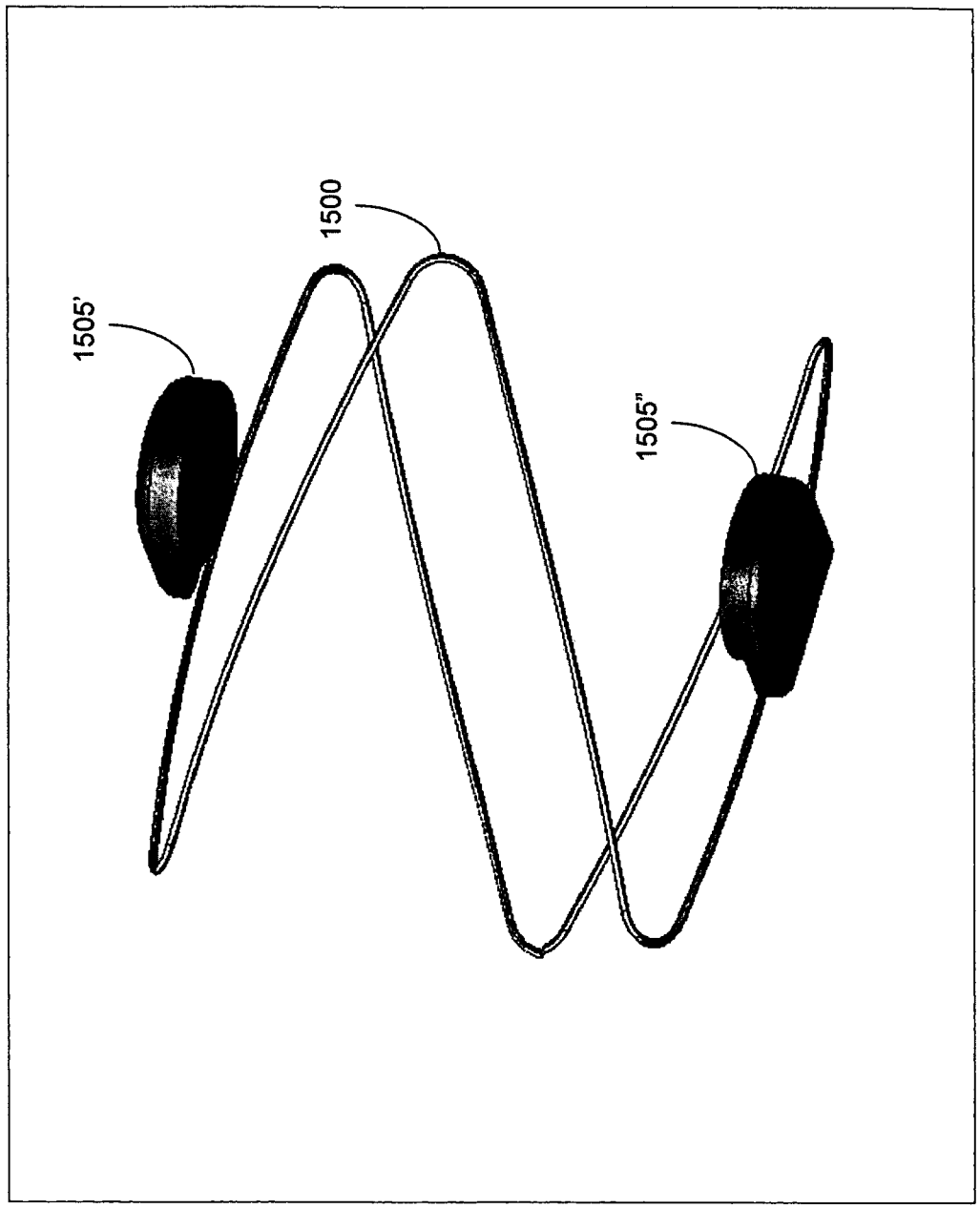
FIG. 15A is a perspective view of one portion of a magnetically-coupled wave anchor device.
Figure 15B:
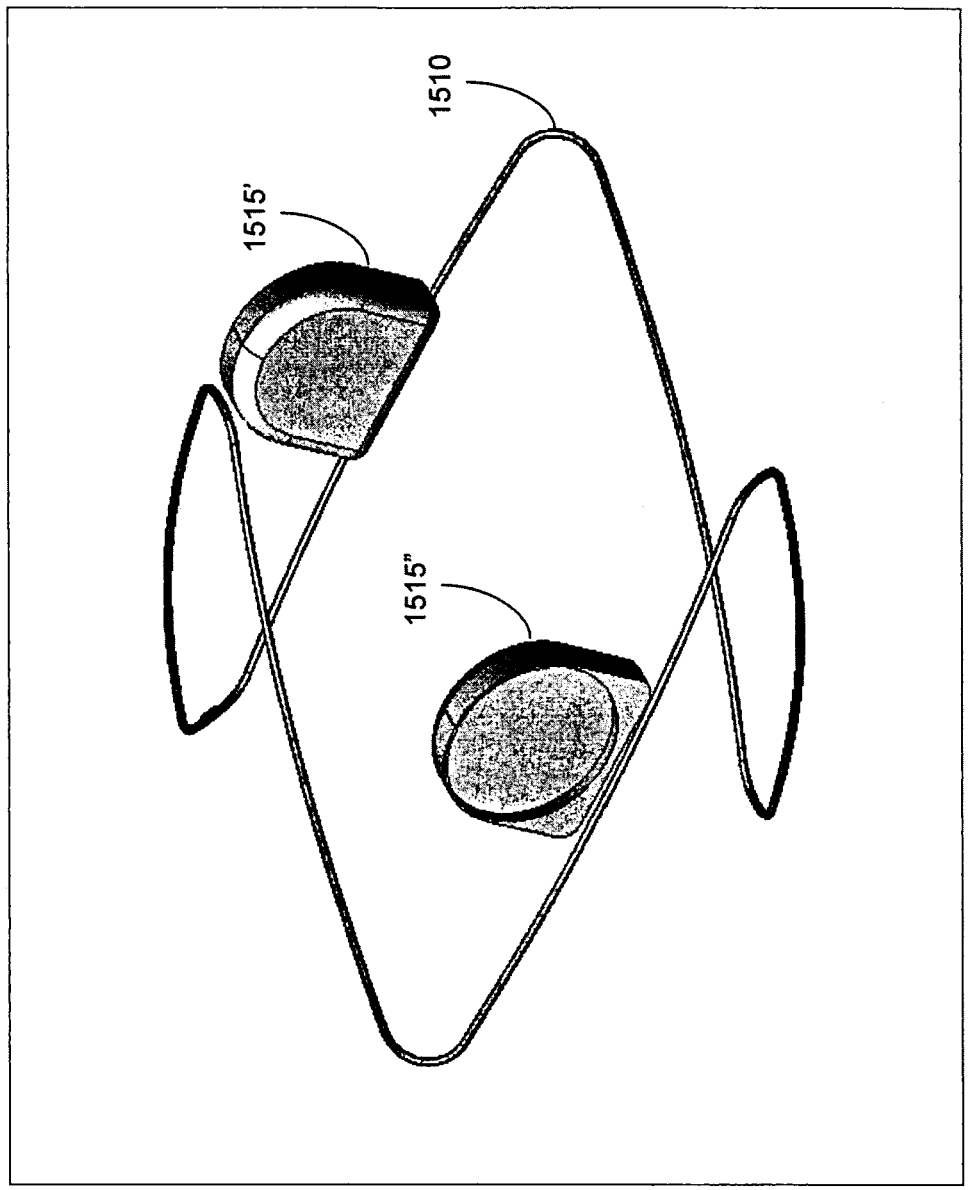
FIG. 15B is a perspective view of a mating portion of the magnetically-coupled wave anchor device of FIG. 15A.
Figure 15C:
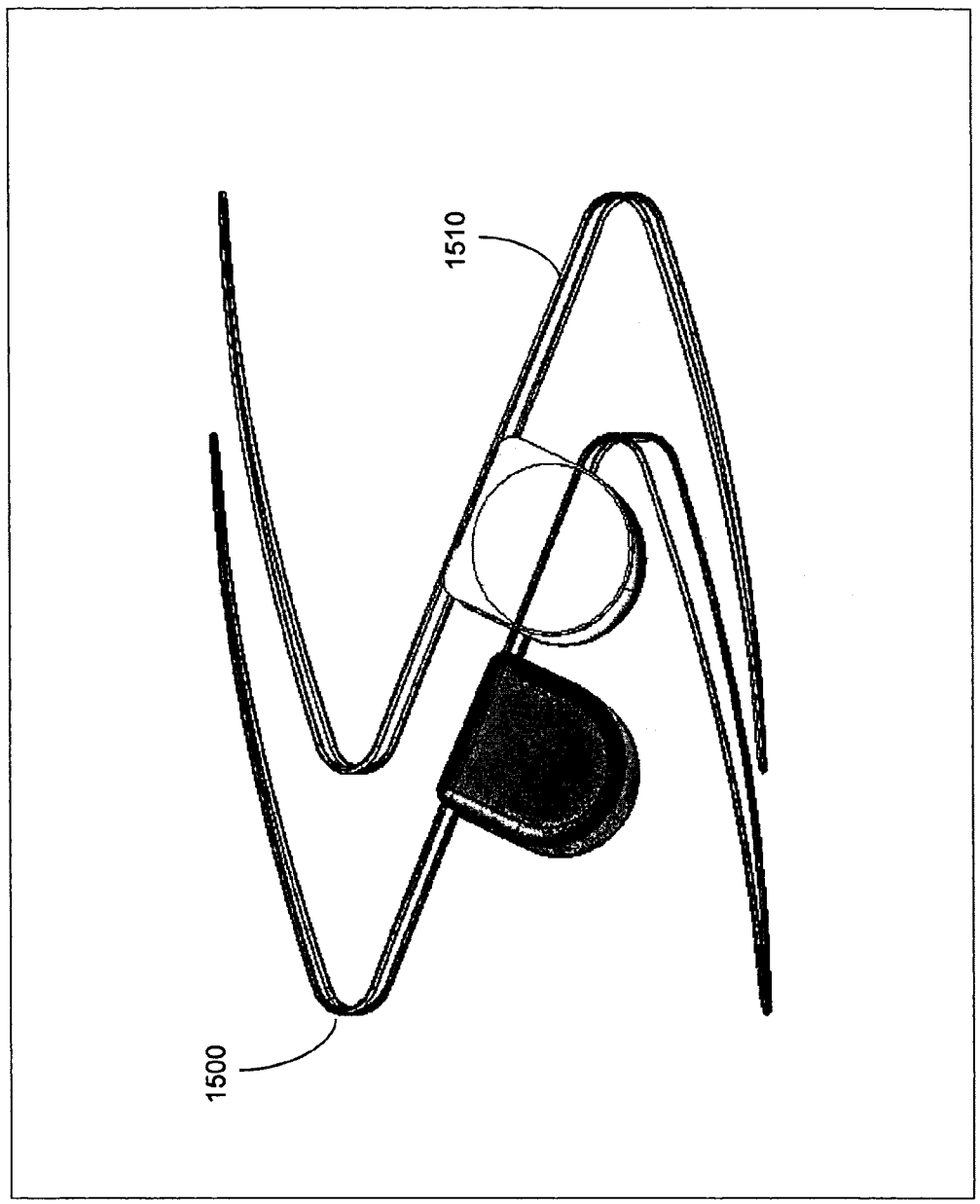
FIG. 15C is a side view of both portions of the magnetically-coupled wave anchor device shown in an uncoupled configuration.
Figure 15D:
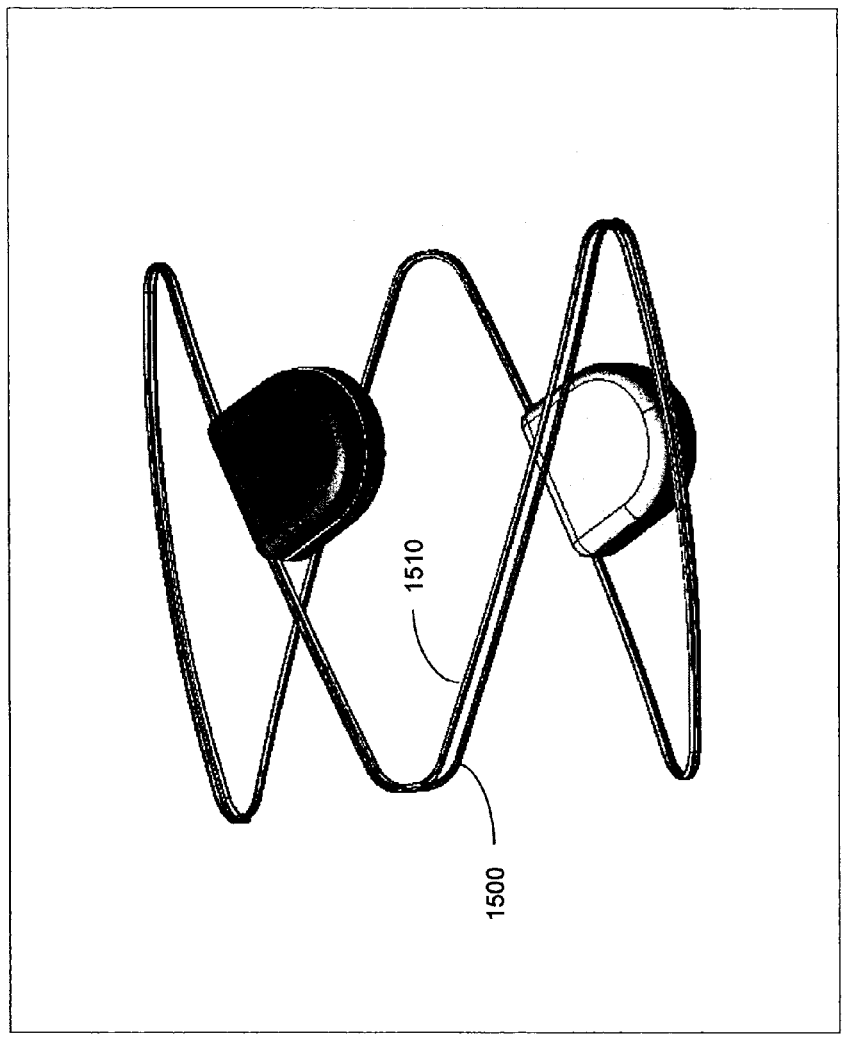
FIGS. 15D and 15E are respectively a side and end view of a magnetically-coupled wave anchor device shown in a coupled configuration.
Figure 15E:
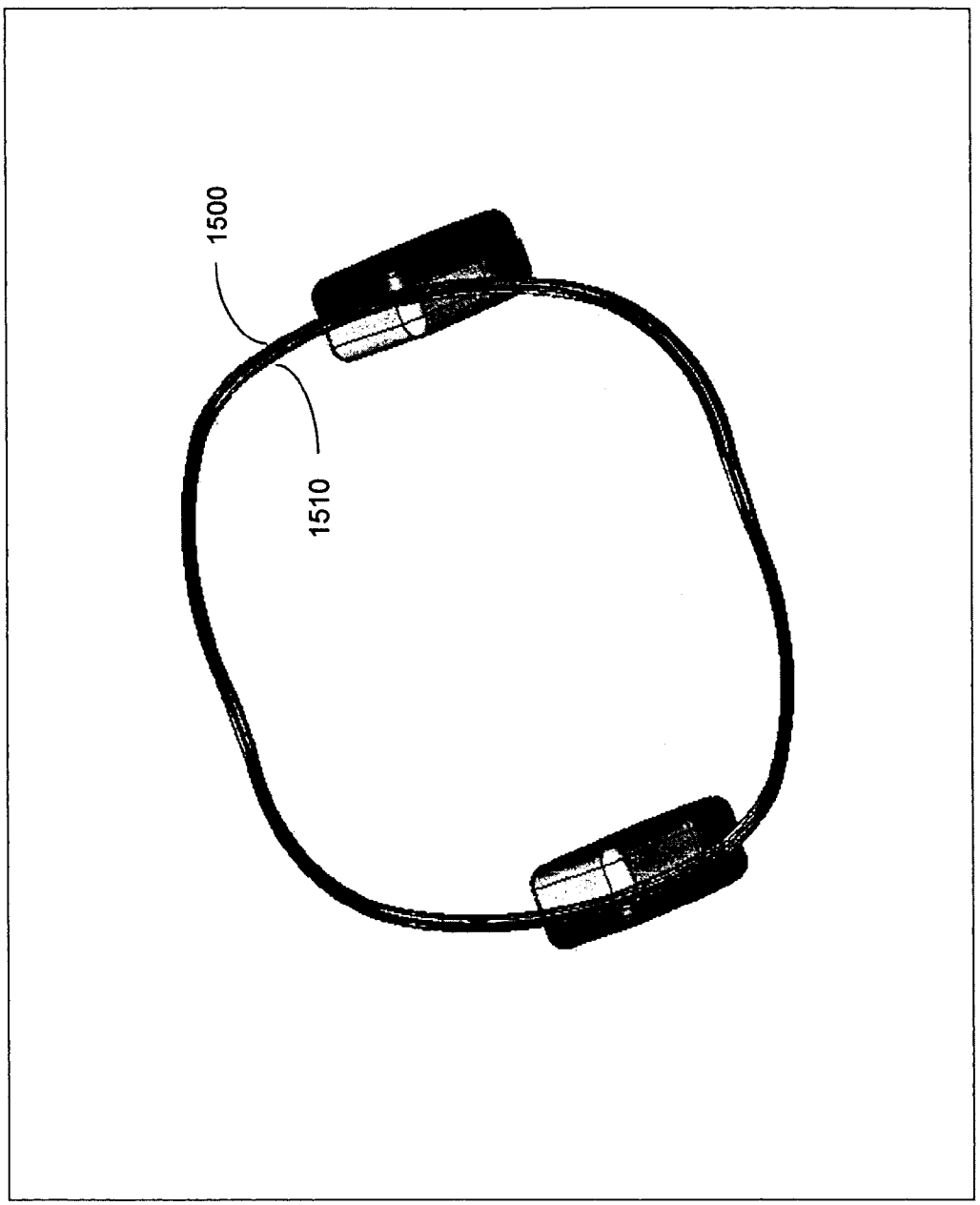

In one embodiment illustrated in FIGS. 15A-15E, a first anchor component 1500 can be secured to an internal lumen of the gastrointestinal tract using any of the above-described means. The first anchor component 1500 includes a first and a second magnets 1505', 1505". The second anchor component 1510 can be secured to a medical device, such as an elongated sleeve. The second anchor component 1510 includes a first and a second magnetically-attracted feature 1515', 1515". The two anchor components 1500, 1510 when brought into proximity with each other as shown in FIG. 15C magnetically couple together as described above. A side view and an end view of the coupled anchors 1500, 1510 are respectively shown in FIGS. 15D and 15E.

Figure 16:
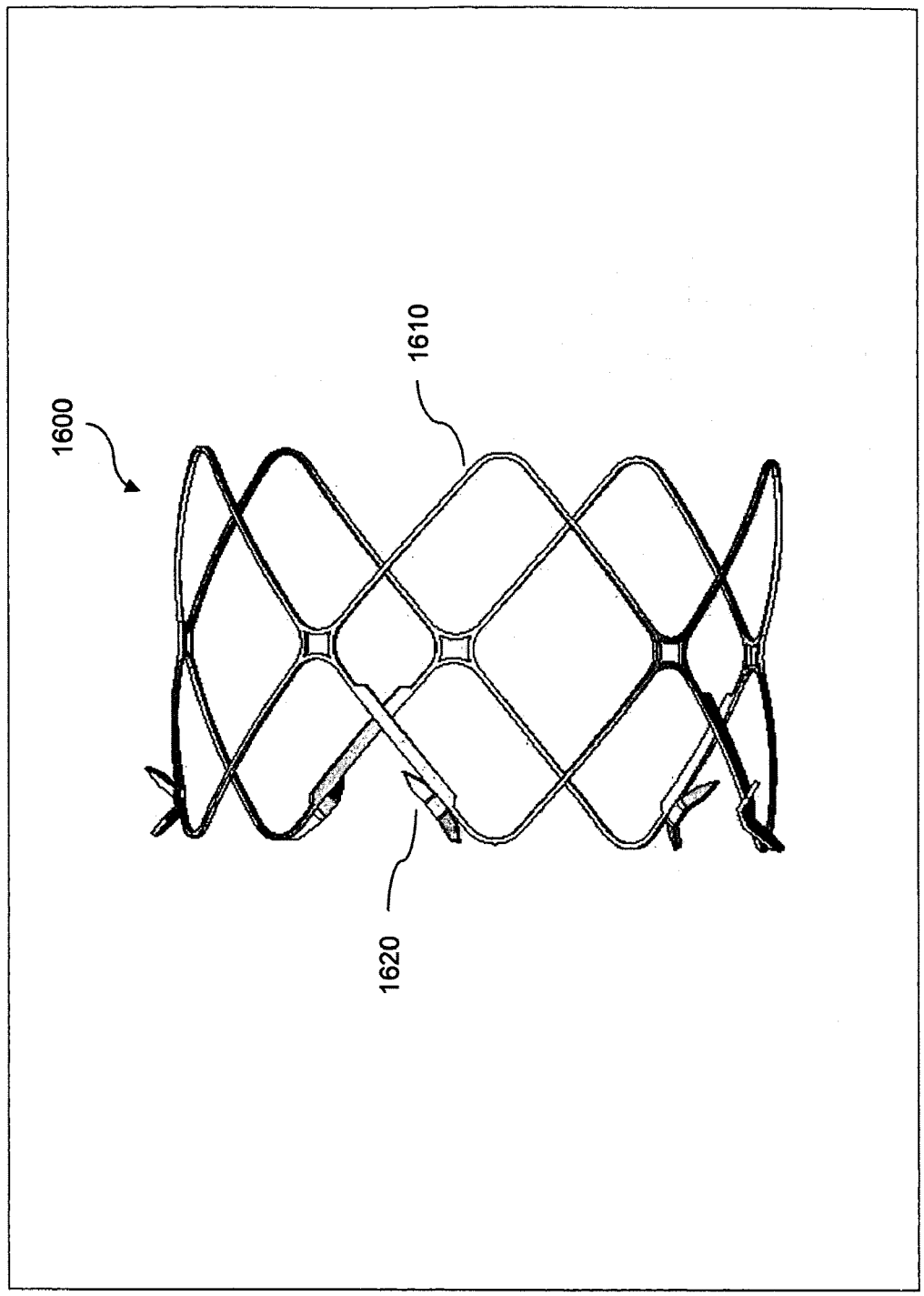
FIG. 16 shows one embodiment of the invention including barbs that are integrally-formed.
Figure 17:
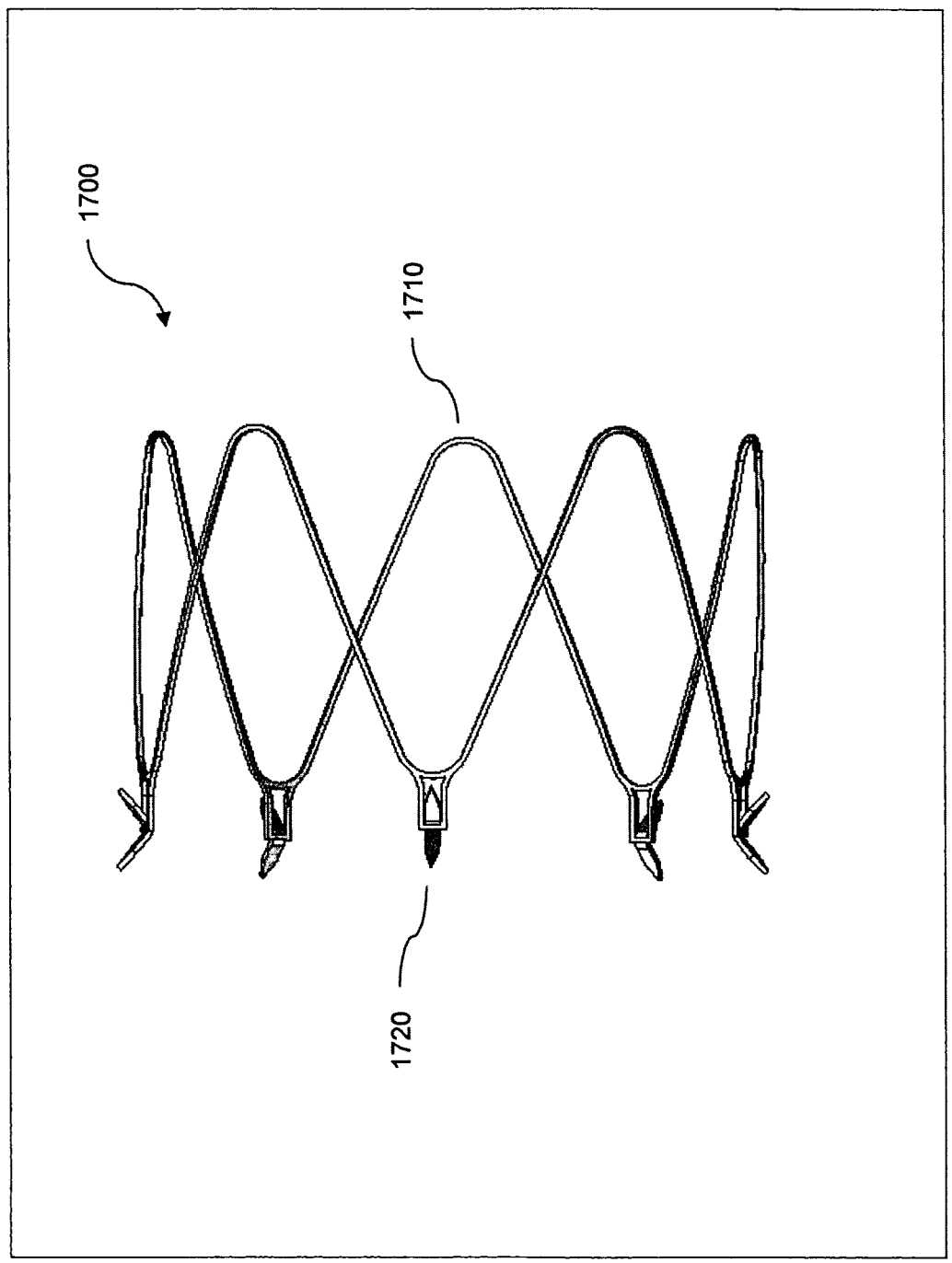
FIG. 17 shows an alternative embodiment of the invention including barbs that are integrally-formed.

In some embodiments, the wave anchor is formed from a wire or cable strand. In other embodiments, as shown in FIGS. 16 and 17, the wave anchor can be cut from tubular stock. For example, the wave anchor can be laser cut from a Nitinol tube. Advantageously, the wave pattern can be formed so that a number of substantially identical wave anchors can be cut from the same tube with minimal waste. Further, mechanical fasteners, such as barbs or staples can also be cut from the same tube, so that the wave anchor and the barbs are contiguous. When formed in this manner, the barbs would be bent or angled away from the axis of the wave anchor to engage muscular tissue as described above generally.

While this invention has been particularly shown and described with references to preferred embodiments thereof, it will be understood by those skilled in the art that various changes in form and details may be made therein without departing from the scope of the invention encompassed by the appended claims.

What is claimed is:

1. A gastrointestinal implant device comprising:
   an unsupported, flexible sleeve, open at both ends, and adapted to extend into the intestine; and
   a wave anchor coupled to a proximal portion of the sleeve, the wave anchor having only a single wave in only a single revolution formed of an elongated resilient member, the single wave having an axial length within a range of about 25 millimeters to about 50 millimeters, the wave anchor defining a central lumen and accommodating a diameter of an adult human's intestine of about 45 millimeters, and the wave anchor being adapted for attachment within an animal body,
   there being no wave of elongated resilient member in the gastrointestinal implant device other than said single wave.

2. The gastrointestinal implant device of claim 1, wherein the wave anchor is adapted for attachment in the intestine.

3. The gastrointestinal implant device of claim 2, wherein the wave anchor is adapted for attachment in the duodenum.

4. The gastrointestinal implant device of claim 2, wherein the wave anchor is adapted for attachment in the duodenal bulb.

5. The gastrointestinal implant device of claim 1, wherein the wave anchor is adapted for removable attachment in the intestine.

6. The gastrointestinal implant device of claim 1, wherein the elongated resilient member is formed about a central axis of the central lumen, the resilient member defining an oscillating pattern about the central axis alternating between proximal and distal ends of the wave anchor.

7. The gastrointestinal implant device of claim 6, wherein the wave pattern has at least four oscillations.

8. The gastrointestinal implant device of claim 6, wherein the resilient member comprises a material selected from the group consisting of: metals, alloys, plastics, and combinations thereof.

9. The gastrointestinal implant device of claim 6, wherein the resilient member comprises a super elastic alloy.

10. The gastrointestinal implant device of claim 9, wherein the super elastic alloy is a Nickel-Titanium alloy.

11. The gastrointestinal implant device of claim 6, wherein the elongated resilient member includes a plurality of filaments.

12. The gastrointestinal implant device of claim 11, wherein some of the plurality of filaments have different physical properties.

13. The gastrointestinal implant device of claim 6, wherein the resilient member comprises a first length having an associated physical property and a second length having a different associated physical property.

14. The gastrointestinal implant device of claim 13, wherein the physical property is resiliency.

15. The gastrointestinal implant device of claim 13, wherein the physical property is thickness.

16. The gastrointestinal implant device of claim 13, wherein the physical property is cross-sectional profile.

17. The gastrointestinal implant device of claim 1, wherein the axial length is between about 31.25 millimeters and about 37.5 millimeters.

18. The gastrointestinal implant device of claim 1, further comprising a feature for attaching the wave anchor within a natural lumen of the gastrointestinal tract.

19. The gastrointestinal implant device of claim 18, wherein the feature for attaching is selected from the group consisting of: mechanical fasteners, chemical fasteners, and combinations thereof.

20. The gastrointestinal implant device of claim 19, wherein the chemical fastener includes a surgical adhesive.

21. The gastrointestinal implant device of claim 18, wherein the feature for attaching is selected from the group consisting of: barbs, sutures, staples, and combinations thereof.

22. The gastrointestinal implant device of claim 1, wherein the implant device is attached using a first plurality of barbs.

23. The gastrointestinal implant device of claim 22, wherein each of the plurality of barbs comprises an elongated member, attached at one end to the wave anchor, the other end extending generally outward from the central axis, the barb sized to engage muscular tissue of the surrounding intestine.

24. The gastrointestinal implant device of claim 22, wherein the plurality of barbs are erodible.

25. The gastrointestinal implant device of claim 22, wherein the first plurality barbs are axially distributed and located substantially at one of the ends of the device.

26. The gastrointestinal implant device of claim 25, further comprising a second plurality of axially-distributed barbs located between the first plurality of barbs and the other end of the device.

27. A gastrointestinal implant device comprising:
    an unsupported, flexible sleeve, open at both ends, and adapted to extend into the intestine; and
    an anchor coupled to a proximal portion of the sleeve, the anchor adapted for engaging a wall of a gastrointestinal tract within an animal body, the anchor having only a single annular wave pattern formed of an elongated resilient member in only a single revolution about a central axis, and the annular wave pattern defining an oscillating pattern about the central axis alternating between first and second axial ends of the anchor, the first and second axial ends being separated by an axial length that is within a range of about 25 millimeters and about 50 millimeters, the anchor defining a central lumen and accommodating a diameter of an adult human's intestine of about 45 millimeters.

28. A gastrointestinal implant device comprising:

flexible sleeve means, open at both ends, for extending into the intestine of an animal body; and wave anchor means for attaching a proximal portion of the sleeve within the animal body, the wave anchor means having only a single wave in only a single revolution of an elongated resilient member, the single wave having an axial length of within a range of about 25 millimeters and about 50 millimeters, the wave anchor defining a central lumen and accommodating a diameter of an adult human's intestine of about 45 millimeters, there being no wave of elongated resilient member in the gastrointestinal implant device other than said single wave.

* * * * *